United States Patent [19]

Sholder

[11] Patent Number: 5,334,220
[45] Date of Patent: Aug. 2, 1994

[54] DUAL-CHAMBER IMPLANTABLE PACEMAKER HAVING AN ADAPTIVE AV INTERVAL THAT PREVENTS VENTRICULAR FUSION BEATS AND METHOD OF OPERATING SAME

[75] Inventor: Jason A. Sholder, Northridge, Calif.

[73] Assignee: Siemens Pacesetter, Inc., Sylmar, Calif.

[21] Appl. No.: 976,153

[22] Filed: Nov. 13, 1992

[51] Int. Cl.$^5$ ............................................. A61N 1/362
[52] U.S. Cl. ................................................... 607/9
[58] Field of Search ................................. 128/419 PG

[56] References Cited

U.S. PATENT DOCUMENTS

| | | | |
|---|---|---|---|
| 4,429,697 | 2/1984 | Nappholz et al. | 128/419 |
| 4,554,921 | 11/1985 | Boute et al. | 128/419 |
| 4,712,555 | 12/1987 | Thornander et al. | 128/419 |
| 4,722,341 | 2/1988 | Hedberg et al. | 128/419 |
| 4,788,980 | 12/1988 | Mann et al. | 128/419 |
| 4,847,617 | 7/1989 | Silvian | 340/870 |
| 4,940,052 | 7/1990 | Mann et al. | 128/419 |
| 4,944,298 | 7/1990 | Sholder | 128/419 |
| 4,974,589 | 12/1990 | Sholder | 128/419 |
| 5,086,774 | 2/1992 | Duncan | 128/419 |
| 5,144,950 | 9/1992 | Stoop et al. | 128/419 |

*Primary Examiner*—William E. Kamm
*Attorney, Agent, or Firm*—Bryant R. Gold; Samuel M. Katz; Malcolm J. Romano

[57] ABSTRACT

A dual-chamber implantable pacemaker automatically adjusts its AV interval so that any ventricular stimulation pulses generated by the pacemaker at the conclusion of the pacemaker-defined AV interval occur at a time in the cardiac cycle that avoids fusion with the natural ventricular depolarization of a patient's heart. The AV interval is set using a search sequence that sets the AV interval value to be on one side or the other of the natural conduction time of the heart, and incrementally changes the AV interval value until it crosses over the natural conduction time interval. The cross-over point is manifest by the occurrence of an R-wave, where an R-wave had previously been absent, or the absence of an R-wave, where an R-wave had previously been present. A final AV interval value is then set as the AV interval value at the cross-over point, adjusted by appending an AV margin thereto. The search sequence is automatically invoked whenever a prescribed search time has elapsed, or whenever the sudden presence or absence of a sensed R-wave indicates a sufficient change in the natural conduction time so as to have crossed over with the existing AV interval. If the search sequence is invoked too frequently, it is automatically suspended for a prescribed suspension period.

23 Claims, 7 Drawing Sheets

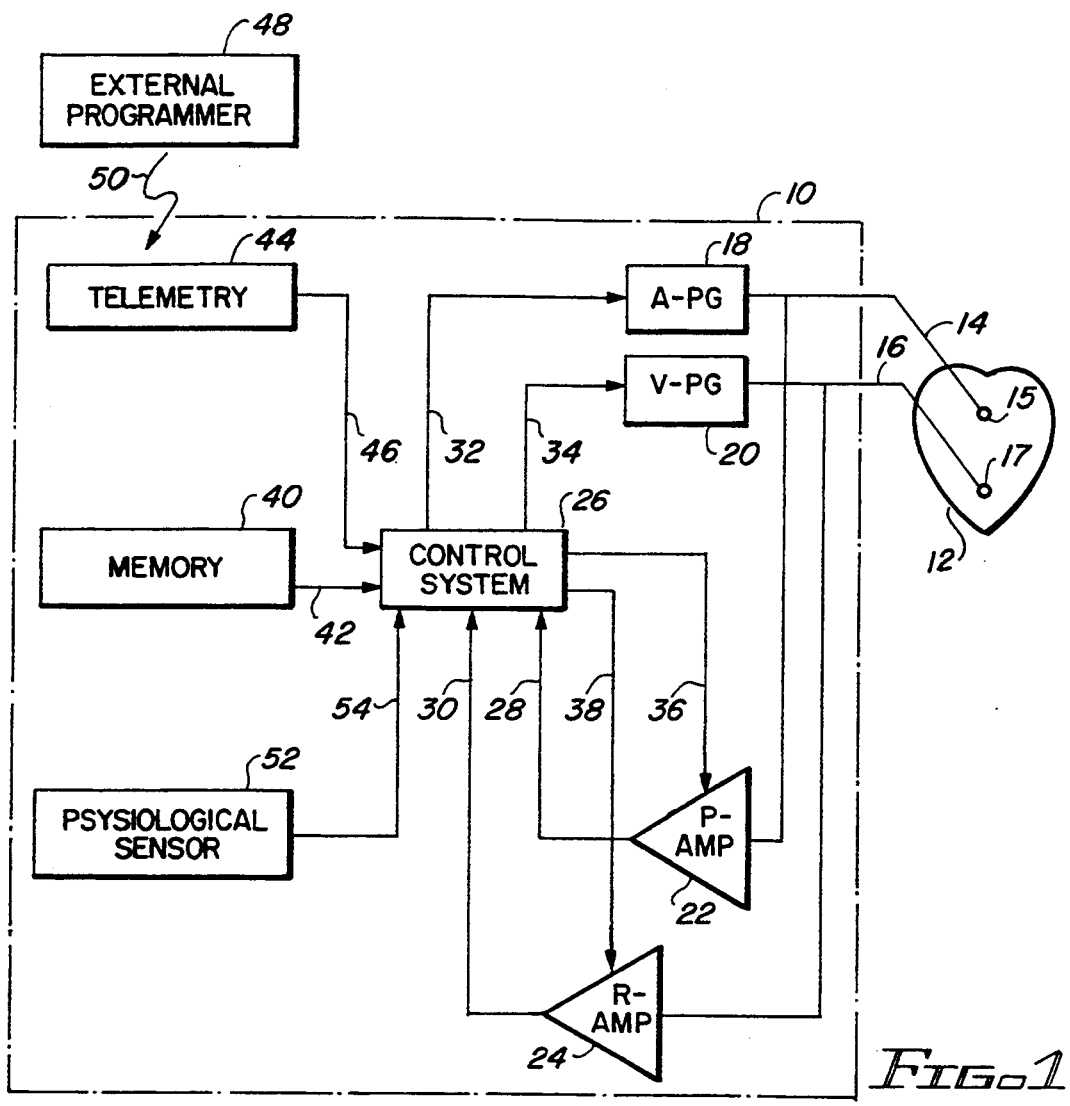
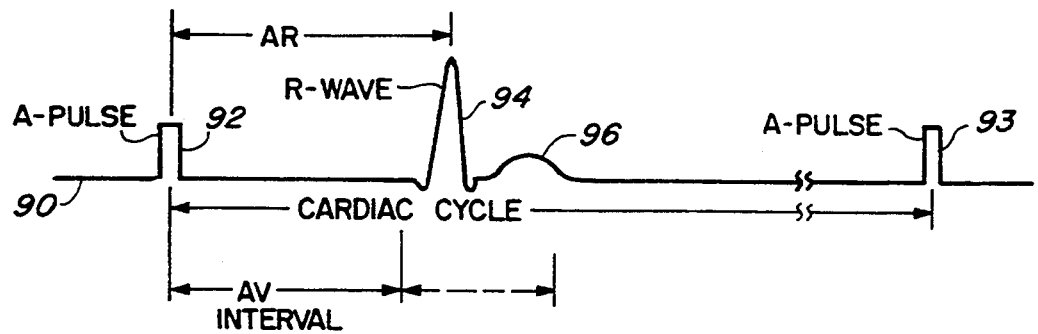

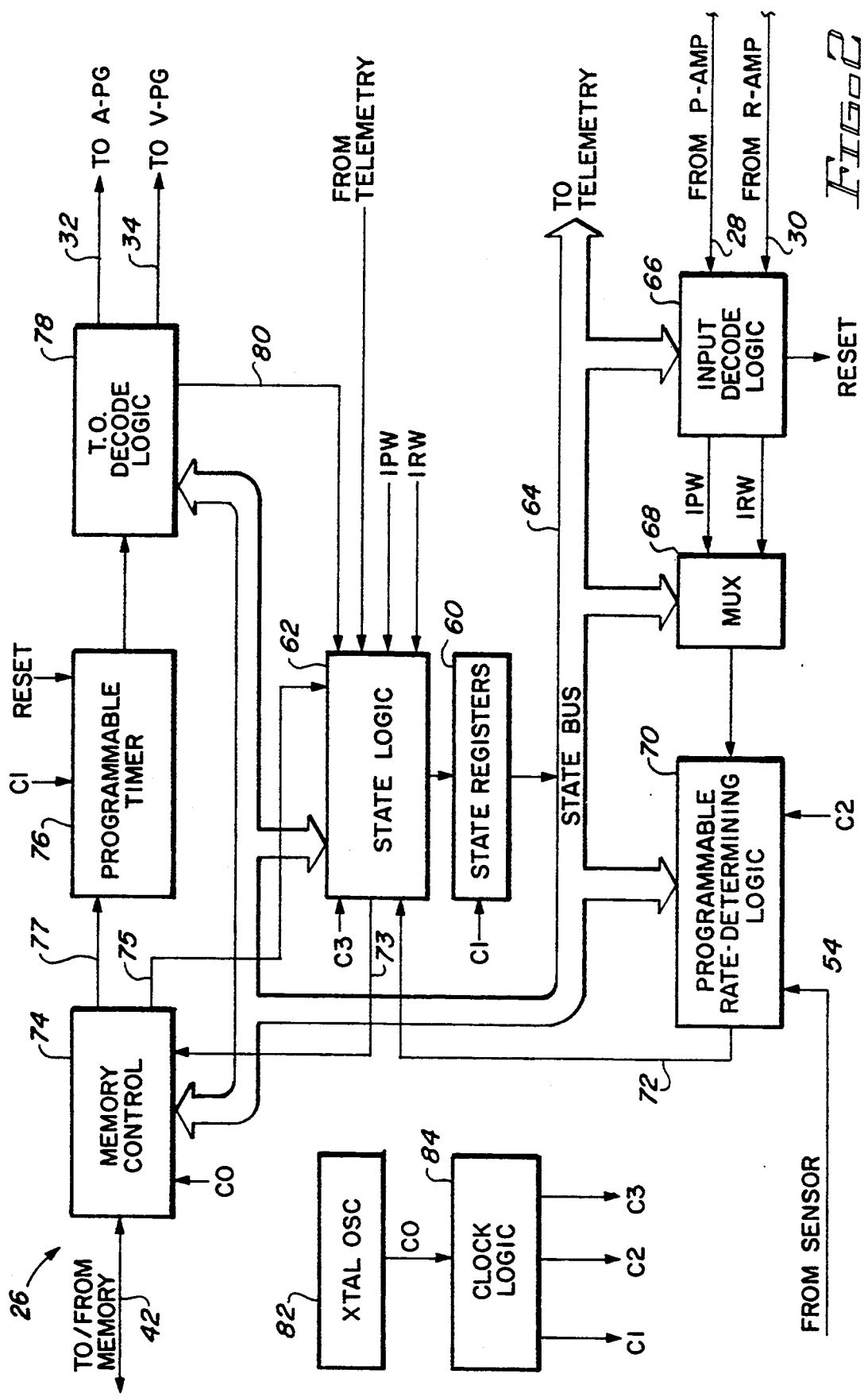

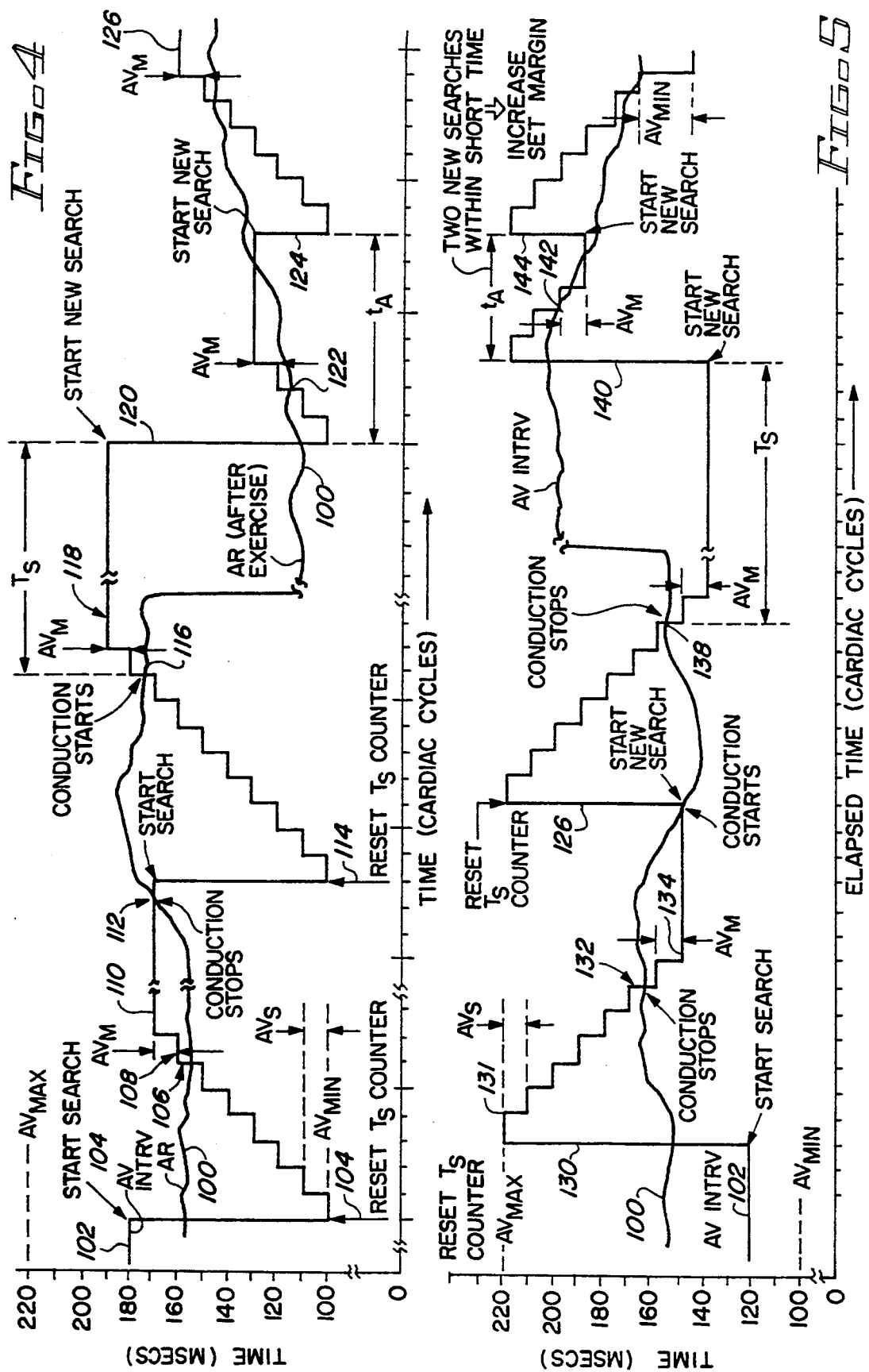

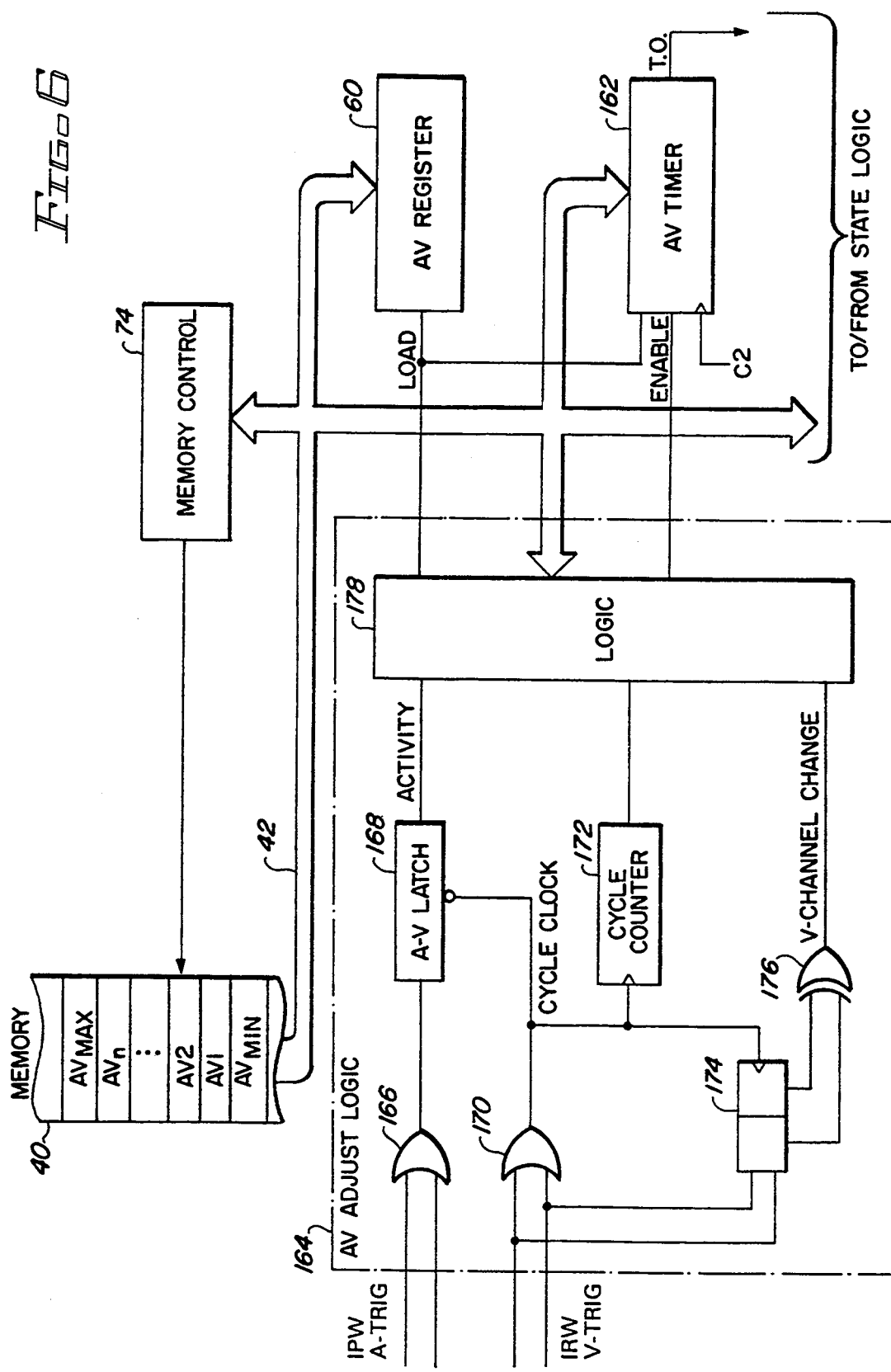

DUAL-CHAMBER IMPLANTABLE PACEMAKER HAVING AN ADAPTIVE AV INTERVAL THAT PREVENTS VENTRICULAR FUSION BEATS AND METHOD OF OPERATING SAME

BACKGROUND OF THE INVENTION

1. Field of the Invention

The present invention relates to implantable medical devices and methods, and more particularly, to an implantable dual-chamber pacemaker that automatically adapts its atrioventricular (AV) delay, or AV interval, in order to avoid fusion beats.

The heart is a pump that pumps life-sustaining blood throughout the body of the patient. The human heart comprises a left side and a right side with each side having a first chamber known as the atrium, and a second chamber known as the ventricle. The atrium receives blood returning from other body locations. At an appropriate time, determined by the sinoatrial (SA) node, an electrical stimulus is provided that causes the muscle tissue surrounding the atrium to depolarize. Depolarization of the atrial muscle tissue is manifest by the occurrence of an electrical signal known as the P-wave. Immediately following the P-wave, the atrial muscle tissue physically contracts, forcing the blood held in the atrium through a one-way valve into the ventricle. The SA node stimulus that caused the atrium to depolarize also travels to the ventricle through the atrioventricular (AV) node and the atrioventricular (AV) bundle. The AV node is a mass of modified heart muscle situated in the lower middle part of the right atrium. It receives the impulse to contract from the sinoatrial node, via the atria, and transmits it through the atrioventricular bundle to the ventricles. The AV bundle is a bundle of modified heart muscle fibers (Purkinje fibers) that pass from the AV node forward to the septum between the ventricles, where it divides into right and left bundles, one for each ventricle. The fibers thus transmit the SA node stimulus from the atria, via the AV node, to the ventricles. However, as the SA node stimulus travels through the AV bundle, it is delayed by an amount commensurate with the same time it should take the blood to physically flow from the atrium to the ventricle.

After the delay through the AV bundle, which delay is referred to herein as the "natural conduction time" of the heart, the SA node stimulus arrives at the ventricular muscle tissue, causing it to depolarize. Depolarization of the ventricular muscle tissue is manifest by the occurrence of an electrical signal known as the R-wave (sometimes referred to as the QRS complex). Immediately following the R-wave, the ventricular muscle tissue physically contracts, forcing the blood held therein through one or more arteries to various body locations. In this manner, then, the heart "beats" or pumps blood by having the atria contract at a rate determined by the SA node, and after the natural conduction time, by having the ventricles contract. After a longer delay, when the atrium has refilled with blood returning from throughout the body, the process repeats.

The heart of a typical healthy patient may beat 60–70 times per minute when the patient is at rest. When the patient is undergoing significant physiological stress, as occurs, e.g., during physical exercise, the rate at which the heart beats, the "heart rate," increases significantly, e.g, up to 150–170 times per minute. The above-described process wherein the atria and ventricles sequentially depolarize and contract in order to pump blood and get ready to depolarize again, is referred to herein as the "cardiac cycle." A given cardiac cycle thus includes one R-wave (or equivalent ventricular activity evidencing depolarization of the ventricles) and one P-wave (or equivalent atrial activity evidencing depolarization of the atria). The length of the cardiac cycle (which represents the period of the heart rate) may be measured as the time interval between successive P-waves or R-waves, although R-waves are usually used because they are easier to detect.

A pacemaker is an implantable medical device that monitors the activity of the heart for the occurrence of P-waves and/or R-waves, and steps in with electronically generated stimuli, when needed, to force the depolarization of the atria and/or ventricles. A pacemaker-generated stimulus that is delivered to the atrium is referred to herein as an "A-pulse." A pacemaker-generated stimulus that is delivered to the ventricle is referred to herein as a "V-pulse." Most pacemakers are configured to provide an A-pulse and/or V-pulse only if a prescribed period of time has elapsed without the occurrence of a P-wave and/or an R-wave, i.e., without the occurrence of natural heart beats.

The prescribed period of time used by the pacemaker between contraction of the ventricle and contraction of the atrium is generally referred to as the V-A Interval, or the atrial escape interval. For most dual-chamber pacemaker modes of operation, only if a P-wave does not occur during the atrial escape interval will the pacemaker step in at the conclusion of such interval and generate an A-pulse.

The prescribed period of time used by the pacemaker between contraction of the atrium and contraction of the ventricle is referred to as the "AV interval," or sometimes it is called the "AV Delay." The pacemaker, for most dual-chamber modes of operation, generates a V-pulse only if the AV Interval elapses without the occurrence of an R-wave.

In the above-described manner, the heart is thus afforded as much time as possible to beat on its own before the electronically-generated stimuli of the pacemaker are delivered to the heart, causing it to beat at the rate set by the pacemaker.

When a pacemaker is first implanted in a patient, or thereafter, the value of the AV interval is set by an attending physician or cardiologist to a value that is selected to optimally assist the patient's heart as it performs its critical function of a pump. For many patients, such AV interval value is a value that is somewhat longer than the natural conduction time of the heart, thereby affording the patient's heart as long a time period as possible before stepping in with the pacemaker generated stimulation pulse (V-pulse). Such action further serves to lengthen the battery life of the pacemaker, because it reduces the number of stimulation pulses that the pacemaker generates, and thereby conserves the limited energy available in the pacemaker battery. However, for other patients, it may be desirable to set the AV interval value at a value that is less than the natural conduction time of the heart, thereby assuring that a V-pulse is generated with most every cardiac cycle. Such patients typically suffer from a cardiomyopathy condition, and the repeated stimulus improves the ability of the ventricular tissue to produce an effective contraction. See Applicant's copending application entitled IMPLANTABLE PACEMAKER HAVING ADAPTIVE AV INTERVAL FOR PROVIDING VENTRICULAR PACING, Ser. No. 07/975,747, filed Nov. 13, 1992, which application is incorporated herein by reference.

Unfortunately, while the AV interval of a pacemaker can be programmably set to a desired value, the natural conduction time of the patient may vary, either with time, or with the medical or physiological condition of the patient. For example, the natural conduction time may vary as a function of whether the patient is undergoing physiological stress (e.g., exercise), or whether the patient is under the influence of medication. In most instances, it is desirable to have the AV interval closely mimic the natural conduction time, because such natural conduction time normally represents the optimum timing between depolarization of the atria and depolarization of the ventricles. However, when the natural conduction time is varying, it is not possible for the AV interval of the pacemaker to mimic such time. What is needed, therefore, is an implantable pacemaker that automatically adjusts its AV interval to a value that tracks or mimics changes in the natural conduction time.

However, it is important to note that the AV interval cannot be set to the same value as the natural conduction time, else the V-pulse will be generated at the same time that the R-wave occurs, a condition known as "fusion." Fusion is not necessarily harmful to the heart, but it represents the expenditure of wasted energy, as the cardiac tissue is not capable of responding to the V-pulse stimulus when it is refractory. The cardiac tissue is refractory concurrent with and/or immediately following depolarization, and remains refractory until the occurrence of the T-wave. Thus, in order to conserve the limited energy of the pacemaker, it is important that fusion be avoided, and that the V-pulse not be applied to the cardiac tissue while it is refractory, i.e., concurrent with and/or immediately following the occurrence of an R-wave. However, if the natural conduction time varies, as it does, it is quite probable that the natural conduction time will wander into the AV interval time, causing fusion to occur. Thus, what is needed is not only an implantable pacemaker that automatically adjusts its AV interval to track or mimic the natural conduction time, but that adjusts the AV interval to a value that is close to, but not the same as, the natural conduction time, thereby providing the desired tracking while avoiding fusion with the natural depolarization of the patient's heart.

Pacemakers are known in the art that automatically adjust various timing intervals, usually the pacemaker-defined atrial escape interval so as to vary the pacing rate to best suit the sensed physiological needs of the patient. However, care must be exercised when the timing intervals of the pacemaker are varied to prevent the development of cardiac arrhythmias, many of which are actually sustained by the adjustable timing provisions of the pacemaker. It would generally be preferable that a timing change be made quickly, and that it be checked and readjusted often, so as to avoid triggering or sustaining cardiac arrhythmias. What is needed, therefore, is a pacemaker that will not only quickly search for and find the desired AV interval value, but that will automatically detect when an adjustment of the AV interval is needed, or not needed. It would also be desirable if the adjustment of the AV interval could be automatically suspended if it was determined that the adjustment was somehow detrimental to the patient or was occurring at a too frequent rate.

SUMMARY OF THE INVENTION

The present invention addresses the above and other needs by providing a dual-chamber implantable pacemaker that automatically adjusts its AV interval so that any ventricular stimulation pulses (V-pulses) generated by the pacemaker at the conclusion of the pacemaker-defined AV interval (or AV delay) occur at a time in the cardiac cycle that avoids fusion with the natural ventricular depolarization of a patient's heart. As indicated above, a natural ventricular depolarization occurs at the conclusion of the natural conduction time of the heart, and is manifest by the occurrence of an R-wave. The natural conduction time comprises that time interval from the onset of atrial activity to the depolarization of the ventricular muscle tissue, i.e., to the occurrence of an R-wave. The present invention thus adjusts the time when the V-pulse occurs within the cardiac cycle so that it occurs near the same time as an R-wave would occur, but does not occur at the same time as an R-wave.

The pacemaker of the present invention provides an AV interval adjustment sequence that automatically searches for and sets the AV interval value to a value that is close to, but different from, the natural conduction time. The AV interval is set by invoking an AV interval search sequence. Such sequence initially sets the AV interval to a value that is on one side or the other of the natural conduction time, and then incrementally changes the AV interval value, preferably in stair-step fashion, with a new AV interval value being used during each adjustment time period of the search sequence. The adjustment time period includes at least one cardiac cycle. Adjustment of the AV interval continues in the manner described until the AV interval crosses over (becomes less than or greater than) the natural conduction time. The cross over point is manifest by the occurrence of an R-wave, where an R-wave had previously been absent; or the absence of an R-wave, where an R-wave had previously been present. A final AV interval value is then set as the AV interval value at the cross-over point, adjusted by an appropriate AV margin value.

In accordance with one aspect of the present invention, the adjustment time period comprises a single cardiac cycle, and the adjustment sequence is quickly concluded within just a few, e.g., less than 10–15, cardiac cycles. Hence, the AV adjustment can advantageously be invoked quickly and easily, thereby assuring that the AV interval value used by the pacemaker is quickly set to an optimum value.

In accordance with another aspect of the invention, the adjustment sequence is automatically invoked whenever a prescribed search time has elapsed, or whenever the sudden presence or absence of a sensed R-wave indicates a change in the natural conduction time sufficient to have caused a cross over with the existing AV interval. Thus, the present invention advantageously adjusts the AV interval whenever an adjustment is needed.

In accordance with still another aspect of the invention, if the AV interval search sequence is invoked too frequently, it is automatically suspended for a programmable suspension period.

One embodiment of the present invention may be characterized as an implantable pacemaker that includes an atrial channel having atrial sensing means for sensing an atrial depolarization (P-wave), and atrial pacing means for generating an atrial stimulation pulse (A-pulse); as well as a ventricular channel having ventricular sensing means for sensing a ventricular depolarization (R-wave), and ventricular pacing means for generating a ventricular stimulation pulse (V-pulse). The pacemaker further includes a memory circuit wherein operating instructions and control parameters may be stored, and a control system coupled to the memory circuit and the atrial and ventricular channels for coordinating the operation of the atrial and ventricular sensing means, and the atrial and ventricular pacing means in accordance with the programmed operating instructions and control parameters stored in the memory circuit. The control system includes three main components: (1) timing means for: (a) defining an AV interval, (b) defining an atrial escape interval, and (c) measuring a conduction time interval, the conduction time interval comprising the time between sensing or pacing in the atrial channel and the sensing of an R-wave in the ventricular channel; (2) logic means for: (a) generating the V-pulse in the ventricular channel at the conclusion of the AV interval only in the event an R-wave is not sensed during the AV interval, with the AV interval commencing with the occurrence of either a P-wave or an A-pulse in the atrial channel, and (b) generating the A-pulse in the atrial channel at the conclusion of atrial escape interval only in the event a P-wave is not sensed during the atrial escape interval; and (3) adjustment means for automatically adjusting the AV interval to a value that is different than the conduction time interval. Such a pacemaker thus advantageously generates V-pulses, if at all, at a time that is different than the end of the conduction time interval, thereby avoiding fusion between the V-pulses and the R-waves.

The adjustment means included in such a pacemaker may further be characterized as including: (a) means for changing the value of the AV interval from an existing AV interval value to an initial AV adjustment value for a prescribed adjustment time period, and for thereafter changing the value of the AV interval in stair-step fashion, with the AV interval assuming a new AV interval value that is a prescribed incremental difference from a preceding AV interval value for each of a plurality of subsequent adjustment time periods; (b) means for determining if there is a change in the type of ventricular activity, i.e., an R-wave or a V-pulse, that occurs in the most recent adjustment time period compared to the type of ventricular activity that occurred in the adjustment time period just prior to the most recent adjustment time period (where a change in the type of ventricular activity provides an indication that the new AV interval value used in the most recent adjustment time period has just crossed over, i.e, become longer or shorter than, the conduction time interval); and (c) setting a final AV adjustment value as a function of the AV interval value used in the most recent adjustment time period for which a change was detected in the type of ventricular activity that occurred in the ventricular channel.

An additional embodiment of the present invention may similarly be characterized as an implantable dual-chamber pacemaker that automatically adjusts its AV interval and avoids fusion between the generation of a ventricular stimulation pulse (V-pulse), at the conclusion of the AV interval, and the occurrence of natural ventricular depolarization, as evidenced by the occurrence of an R-wave. Such dual-chamber pacemaker includes at least the following elements: (1) means for sensing atrial activity in an atrial channel; (2) means for sensing an R-wave and generating the V-pulse in a ventricular channel; and (3) control means for: (a) defining the AV interval as the longest time interval the pacemaker will allow from the occurrence of atrial activity in the atrial channel until the generation of a V-pulse in the ventricular channel, with the occurrence of an R-wave during the AV interval causing the generation of a V-pulse to be inhibited, (b) recognizing a need to adjust the AV interval from its present value to a new value, (c) adjusting the AV interval from its present value to an intermediate value, when an adjustment in the AV interval is needed, following a prescribed adjustment sequence, (d) determining when in the adjustment sequence the AV interval crosses over an AR interval, the AR interval comprising the time interval between atrial activity in the atrial channel and sensing an R-wave in the ventricular channel, and thereby representing a measure of the natural conduction time of a heart to which the pacemaker is coupled, and (e) setting the new AV value of the pacemaker to a value that is a prescribed difference from the AR interval. Such a pacemaker advantageously ensures that a V-pulse and an R-wave will not occur at the same time, thereby avoiding fusion, even though the AV interval is automatically adjusted when needed.

Another embodiment of the invention may be characterized as a method of operating a dual-chamber pacemaker to avoid fusion between a ventricular stimulus (V-pulse) and an R-wave. The method is used with a pacemaker that has at least: means for sensing atrial activity in an atrial channel; means for sensing an R-wave and generating the V-pulse in a ventricular channel; and control means for defining the AV interval as the longest time interval the pacemaker will allow from the occurrence of atrial activity in the atrial channel until the generation of a V-pulse in the ventricular channel, with the occurrence of an R-wave during the AV interval causing the generation of a V-pulse to be inhibited. The method of operation of such a pacemaker includes the following steps: (a) recognizing a need to adjust the AV interval from its present first value to a final value; (b) adjusting the AV interval from its present value to an adjustment start value; (c) incrementally adjusting the value of the AV interval from its adjustment start value in a direction back towards the first value in prescribed increments, with each prescribed increment comprising a specified change in the duration of the AV interval in the adjustment direction, and with each adjusted value of the AV interval being used in a specified incremental time period that includes at least one cardiac cycle; (d) monitoring the ventricular channel during each of the specified incremental time periods for the occurrence of either an R-wave or the presence of a V-pulse; (e) detecting the approximate duration of an AR interval from the monitoring performed in step (d), the AR interval defining the time period between atrial activity in the atrial channel and the occurrence of an R-wave; and (f) setting the final value of the AV interval to be different from the AR interval detected in step (e). Such method advantageously adjusts the AV interval to a value that avoids fusion between the V-pulse and the R-wave.

It thus a feature of the present invention to provide an implantable pacemaker that automatically adjusts its AV interval to a value that is just less than, or just greater than, the natural conduction time of a patient's heart, thereby mimicking insofar as possible the natural timing associated with the heart.

It is another feature of the invention to provide such adjustment of the AV interval while avoiding fusion, i.e., preventing the issuance of a V-pulse on top of an R-wave, thereby assuring that any V-pulses that are issued are effective at depolarizing the ventricular muscle tissue.

It is an additional feature of the invention to provide an AV interval adjustment sequence, or technique, that quickly and automatically searches for a desired AV interval value—typically a value that is just less than or just greater than the natural condition time interval——and attaches a prescribed margin thereto, thereby assuring that the desired AV interval value is maintained while avoiding fusion. Further, it is a feature of the invention to adaptively change the prescribed margin, as required, in order to minimize the frequency at which the adjustment technique is invoked.

It is yet another feature of the invention to provide an automatic AV interval adjustment procedure that is automatically invoked when needed, and that can be automatically suspended if invoked too often.

BRIEF DESCRIPTION OF THE DRAWINGS

The above and other aspects, features and advantages of the present invention will become more apparent from the Detailed Description of the Invention, presented in conjunction with the following drawings, wherein:

FIG. 1 is block diagram of a dual-chamber programmable pacemaker;

FIG. 2 is a block diagram of one embodiment of the control logic of the pacemaker of FIG. 1;

FIG. 3 diagrammatically illustrates a cardiac cycle and illustrates the manner in which the PV (or AV) interval is adjusted to avoid fusion;

FIG. 4 is a diagram illustrating how the present invention adaptively adjusts the PV (or AV) interval over several cardiac cycles in order to incrementally increase such interval from a minimum value to a value that is greater than the natural conduction time, thereby avoiding fusion;

FIG. 5 is a diagram as in FIG. 4, except that the PV (or AV) interval is incrementally decreased over several cardiac cycles from a maximum value to a value that is less than the natural conduction time, thereby avoiding fusion;

FIG. 6 is a functional block diagram of a portion of the control system of a pacemaker used to carry out an AV interval adjustment of the present invention;

FIGS. 8-1 and 8-2 show a flowchart that illustrates one method that may be used to carry out the adjustment methods illustrated in FIGS. 4 and 5.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

As indicated above, the present invention is directed to an implantable dual-chamber pacemaker, and a method of operating an implantable dual-chamber pacemaker, that automatically adapts or adjusts the AV interval (or PV interval) of the pacemaker in a way that avoids fusion. Automatic adjustment of the AV (or PV) interval is desirable, for example, in order to allow the patient's heart a longer time to beat on its own, even when changes occur in the natural conduction time of a patient. Alternatively, automatic adjustment of the PV (or AV) interval may be desirable in patients suffering from a cardiomyopathy, as disclosed in Applicant's copending patent application, IMPLANTABLE PACEMAKER HAVING ADAPTIVE AV INTERVAL FOR PROVIDING VENTRICULAR PACING, previously cited and incorporated herein by reference.

Throughout the discussion that follows, reference will frequently be made to the AV interval. It is to be understood that all such references to the AV interval also apply to the PV interval, and that whether the AV or PV interval is used depends upon the particular type of atrial activity—an A-pulse or a P-wave—that starts the AV (or PV) interval. Similarly, it is to be understood that any references made to the PV interval also apply to the AV interval. It is further to be understood that when the PV interval is used, it will typically be shorter than the AV interval by a prescribed amount, e.g., 20–40 msec, to account for the latency time involved between applying an A-pulse and having the atrial tissue respond with a depolarization. Those of skill in the art can readily fashion appropriate circuitry to utilize either an AV interval or a PV interval, whichever applies to a given cardiac cycle. For the discussion that follows, then, where reference is made to the AV interval, such AV interval should be considered as the time interval between atrial channel activity, whether such atrial channel activity comprises an A-pulse or a P-wave, and the subsequent delivery of a ventricular stimulation pulse (V-pulse).

Advantageously, the present invention may be implemented using a wide variety of dual-chamber pacemaker configurations and pacemaker hardware. Any pacemaker configuration that allows the pacemaker AV (or PV) interval to be automatically set to a desired value may be used to implement the invention. The description that follows is only exemplary of one such configuration.

Figures 1, 8:
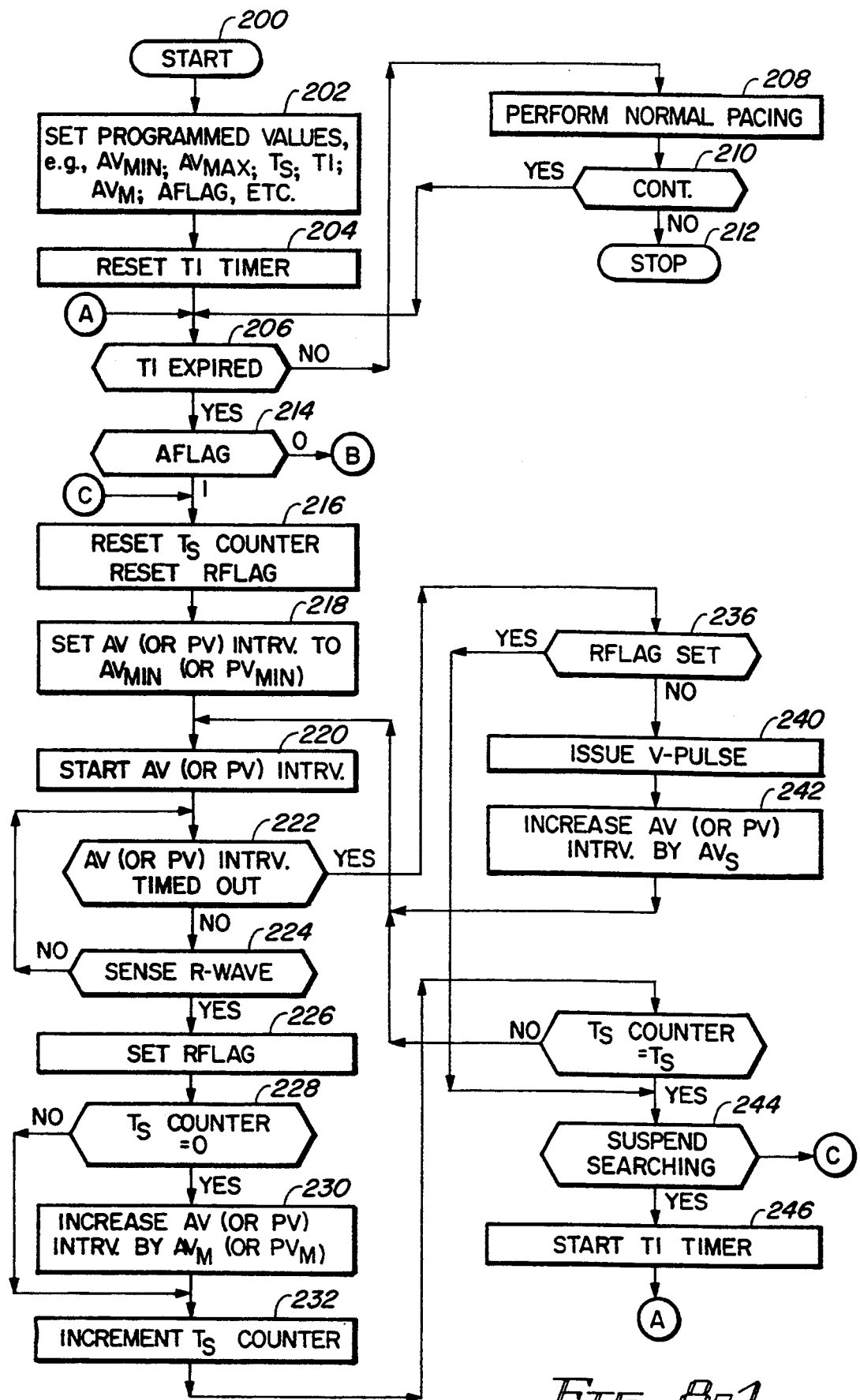

Referring then to FIG. 1, a block diagram of a dual-chamber pacemaker 10 is illustrated. The pacemaker 10 is coupled to a heart 12 by way of leads 14 and 16, the lead 14 having an electrode 15 that is in contact with one of the atria of the heart, and the lead 16 having an electrode 17 that is in contact with one of the ventricles of the heart. The leads 14 and 16 carry stimulating pulses to the electrodes 15 and 17 from an atrial pulse generator (A-PG) 18 and a ventricular pulse generator (V-PG) 20, respectively. Further, electrical signals from the atria are carried from the electrode 15, through the lead 14, to the input terminal of an atrial channel sense amplifier (P-AMP) 22; and electrical signals from the ventricles are carried from the electrode 17, through the lead 16, to the input terminal of a ventricular sense channel amplifier (R-AMP) 24.

Controlling the dual-chamber pacer 10 is a control circuit or control system 26. The control system 26 receives the output signals from the atrial amplifier 22 over signal line 28. Similarly, the control system 26 receives the output signals from the ventricular amplifier 24 over signal line 30. The output signals on signal lines 28 and 30 are generated each time that a P-wave or an R-wave is sensed within the heart 12. The control circuit or system 26 also generates trigger signals that are sent to the atrial pulse generator 18 and the ventricular pulse generator 20 over signal lines 32 and 34, respectively. These trigger signals are generated each time that a stimulation pulse is to be generated by the respective pulse generator 18 or 20. A stimulation pulse generated by the A-PG 18 is referred to as the "A-pulse," and the stimulation pulse generated by the V-PG 20 is referred to as the "V-pulse." During the time that either an A-pulse or V-pulse is being delivered to the heart, the corresponding amplifier, P-AMP 22 and/or R-AMP 24, is typically disabled by way of a blanking signal presented to these amplifiers from the control system over signal lines 36 and 38, respectively. This blanking action prevents the amplifiers 22 and 24 from becoming saturated from the relatively large A-pulse or V-pulse, respectively, that is present at the input terminals of such amplifiers during this time. Such blanking action also helps prevent residual electrical signals present in the muscle tissue as a result of the pacer stimulation from being interpreted as P-waves or R-waves.

Still referring to FIG. 1, the pacer 10 also includes a memory circuit 40 that is coupled to the control system 26 over a suitable data/address bus 42. The memory circuit 40 allows certain control parameters, used by the control system 26 in controlling the operation of the pacemaker, to be programmably stored and modified, as required, in order to customize the pacer's operation to suit the needs of a particular patient. Such data includes the basic timing intervals used during operation of the pacemaker, such as the programmed atrial escape interval (AEI). For purposes of the present invention, such data may also include a family of AV interval data that may be retrieved during an adjustment sequence of the AV interval, as explained more fully below. Further, data sensed during the operation of the pacer may be stored in the memory 40 for later retrieval and analysis.

A telemetry circuit 44 is further included in the pacer 10. This telemetry circuit 44 is connected to the control system 26 by way of a suitable command/data bus 46. In turn, the telemetry circuit 44, which is included within the implantable pacer 10, may be selectively coupled to an external programming device 48 by means of an appropriate communication link 50, which communication link 50 may be any suitable electromagnetic link, such as an RF (radio frequency) channel. Advantageously, through the external programmer 48 and the communication link 50, desired commands may be sent to the control system 26. Similarly, through this communication link 50 and the programmer 48, data (either held within the control system 26, as in a data latch, or stored within the memory 40), may be remotely received from the pacer 10. In this manner, noninvasive communications can be established from time to time with the implanted pacer 10 from a remote, non-implanted location. Many suitable telemetry circuits known in the art that may be used with the present invention for the telemetry circuit 44. See, e.g., U.S. Pat. No. 4,847,617, incorporated herein by reference.

The pacer 10 in FIG. 1 is referred to as a dual-chamber pacemaker because it interfaces with both the atria and the ventricles of the heart. Those portions of the pacer 10 that interface with the atria, e.g., the lead 14, the P-wave sense amplifier 22, the A-pulse generator 18, and corresponding portions of the control system 26, are commonly referred to as the atrial channel. Similarly, those portions of the pacer 10 that interface with the ventricles, e.g., the lead 16, the R-wave sense amplifier 24, the V-pulse generator 20, and corresponding portions of the control system 26, are commonly referred to as the ventricular channel. Throughout the discussion that follows, frequent reference will be made to "atrial channel activity" or "ventricular channel activity." Atrial channel activity thus comprises either the sensing of a P-wave by the sense amplifier 22, or the generating of an A-pulse by the A-pulse generator 18. Similarly, ventricular channel activity comprises either the sensing of an R-wave by the sense amplifier 24 or the generation of a V-pulse by the V-pulse generator 20.

In some pacemakers that implement the present invention, the pacemaker 10 may further include one or more physiological sensors 52 that is connected to the control system 26 of the pacer over a suitable connection line 54. While the sensor 52 is illustrated in FIG. 1 as being included within the pacer 10, it is to be understood that the sensor may also be external to the pacer 10, yet still be implanted within or carried by the patient. A common type of sensor is an activity sensor, such as a piezoelectric crystal, mounted to the case of the pacemaker. Other types of physiologic sensors, such as sensors that sense the oxygen content of blood, respiration rate, pH of blood, body motion, and the like, may also be used in lieu of, or in addition to, an activity sensor. The type of sensor, if any, used is not critical to the present invention. Any sensor or combination of sensors capable of sensing some physiological parameter relatable to the rate at which the heart should be beating can be used. A pacemaker using such sensors is commonly referred to as a "rate-responsive" pacemaker because such a pacemaker adjusts the rate (escape interval) of the pacer in a manner that tracks the physiological needs of the patient.

Figures 2, 8:
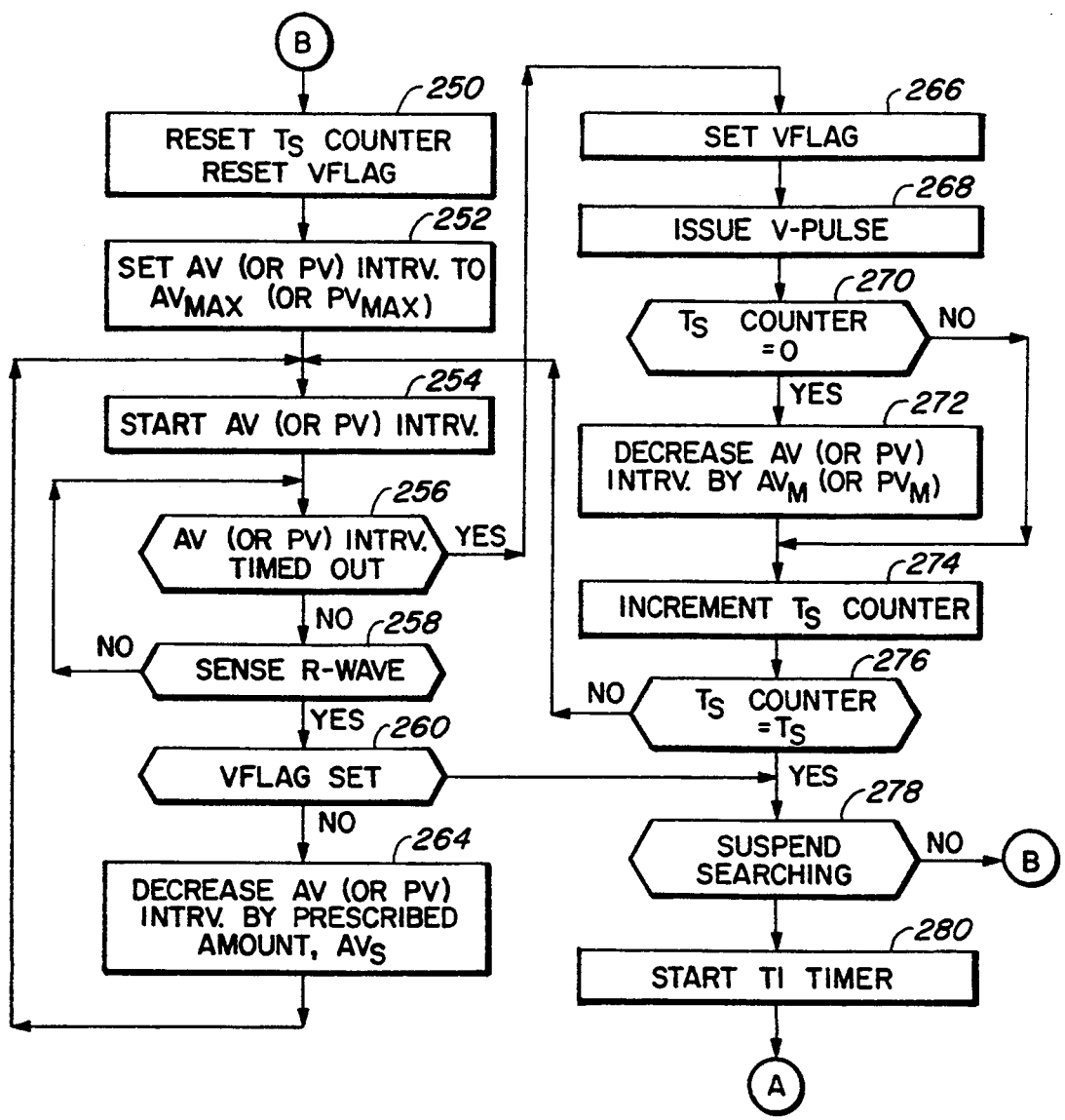

Referring next to FIG. 2, a block diagram of one embodiment of the control circuit or system 26 of the pacer 10 is illustrated. It is noted that other embodiments of a control system 26 may also be utilized, such as a microprocessor-based control system. A representative microprocessor-based system is described, for example, in U.S. Pat. No. 4,940,052, entitled "Microprocessor Controlled Rate-Responsive Pacemaker Having Automatic Threshold Adjustment." The '052 patent is assigned to the same assignee as is this application, and is incorporated herein by reference.

The control system shown in FIG. 2 is based on a state machine wherein a set of state registers 60 define the particular state of the pacer at any instant in time. In general, and as an overview of state machine operation, each state, by design, causes a certain activity or function to be carried out. Several states are executed in a sequence during a given cardiac cycle. The sequence of states that is executed in a particular cardiac cycle is determined by the particular events that occur, such as the sensing of a P-wave or an R-wave, as well as the current state, as certain states can only be entered from certain other states. Only one state can exist at any instant of time, although several different state machines (or control systems) may operate in parallel to control diverse functions. For example, the telemetry circuit 44 (FIG. 1) preferably utilizes its own state machine. The telemetry circuit state machine operates essentially independent of the control system state machine of FIG. 2.

At the heart of the control system 26 is the state logic 62. It is the state logic that controls the "state" of the state registers 60, and hence the function or operation that will next be carried out by the system. The state logic 62 receives as inputs the current state of the state registers, made available over a state bus 64 (which state bus directs the state of the system to several sections of the control system), as well as other signals indicating the current status of the system or events that have occurred. The output signals from the P-AMP 22 (FIG. 1) and the R-AMP 24 (FIG. 1) are directed to an input decode logic circuit 66. This circuit generates appropriate logic signals "IPW" (Inhibiting P-Wave) and "IRW" (Inhibiting R-Wave) that are selected by a multiplexer 68 and sent to rate-determining logic 70. These signals are also sent to the state logic 62. The function of the rate-determining logic 70 is to determine the rate at which either the IPW or IRW signals are occurring. A signal representative of this rate is sent, as an output signal from the rate determining logic 70, to the state logic 62 over signal line 72. Rate-determining logic 70 further receives a sensor rate signal from the sensor 52 (FIG. 1), and (depending upon the particular state of the system, as defined by the state registers 60, and as made available to the rate-determining logic 70 over the state bus 64) sends a rate signal to the state logic 62 over signal line 72 indicative of this sensor rate. Portions of the state logic 62 that have particular applicability to the present invention are included in the description of FIGS. 6 and 7 below.

Still referring to FIG. 2, a memory control circuit 74 provides the needed interface between the circuits of the control system 26 and the memory 40 (FIG. 1). This memory control circuit may be any conventional memory access circuit that sends or receives data to or from memory at a specified address. Data retrieved from memory 40 may be sent to either the state logic 62 (over signal line(s) 75) or to a programmable timer 76 (over signal line(s) 77). Data sent to memory 40 may be either the current state of the system (obtained off of the state bus 64), or other selected signals from the state logic (as made available over signal line(s) 78).

The programmable timer 76 defines a prescribed time interval, the length of which is set by the signal(s) received from the memory control 74 over signal line(s) 77, and the starting point of which begins coincident with the start of the current state, as obtained from the state bus 64. The timer 76 further generates a time-out (T.O.) signal when this prescribed time interval has elapsed. During the prescribed time interval, the timing function may be reset by a reset signal, typically obtained from the input decode logic 66, although some states (as obtained from the state bus 64) may also effectuate an immediate reset of the timer 76. The time-out signal is sent to time-out decode logic 78. It is the function of the time-out decode logic to generate the appropriate trigger signals that are sent to the A-pulse generator 18 or the V-pulse generator 20 (FIG. 1). Further, an appropriate logic signal(s) is sent to the state logic 62 by the time-out decode logic 78 over signal line(s) 80 in order to notify the state logic that the respective trigger signals have been generated. While only a single programmable timer 76 is shown in FIG. 2, it is to be understood that other programmable timers, similar to the timer 76, are also used when there is a need to keep track of more than one time interval at the same time. The timing associated with the AV interval adjustment of the present invention, for example, may use an AV timer as described below in conjunction with FIGS. 6 and 7.

An oscillator 82, preferably a crystal-controlled oscillator, generates a basic clock signal C0 that controls the operation of the system logic. This clock signal C0 is sent to clock logic circuits 84, where other appropriate clock signals, such as clock signals C1, C2 and C3, are generated, all derived from the basic clock signal C0. These clock signals are distributed throughout the control system 26 in order to appropriately synchronize the various events and state changes that occur within the pacemaker. The rate of the basic clock signal C0 is not critical to the present invention. In general, a rate of 25–40 Khz for the basic clock rate C0 is adequate. This rate provides a basic time increment of 25–40 microseconds each clock cycle, and this is more than enough time to effectively control the pacemaker operation. If desired, a faster basic clock rate can be used, particularly by the memory control 74, to speed up the data transfer between the control system 26 and the memory 40, although for most pacemaker operations, a fast data transfer rate is not essential.

In operation, the control system of FIG. 2 starts at an initial state, wherein the state registers 60 assume a prescribed value that defines the initial state. For example, assuming four flip flops are used for the state registers 60, an initial state might be "1000" (hexadecimal "8") wherein the first flip flop assumes a "1" state, and the remaining three flip flops each assume a "0" state. This state may be defined as a V-A Interval (VAI) state wherein a prescribed ventricular-to-atrial (V-A) interval is initiated. For purposes of the present invention, this V-A interval may be considered as the "atrial escape interval," or "AEI." As soon as the memory control 74 detects that the VAI state has been initiated, as evidenced by the "1000" appearing on the state bus 64, it retrieves from the memory 40 or otherwise generates an appropriate data word, previously programmed into the memory 40 from the external programmer 48 or otherwise determined from the pacemaker logic, that defines the desired length of the AEI. This data word is sent to the programmable timer and sets the length of the time period that is to be measured during the VAI state.

The timer 76 is essentially just a counter that counts down (or counts up), using a specified clock signal, to the value specified in the data word. When the counting has been completed, and assuming that the counter has not been reset by the occurrence of a P-wave or other sensed event, the counter or timer 76 is said to have "timed-out," and an appropriate time-out signal is generated and sent to the time-out decode logic 78. The decode logic, in turn, recognizes that the current state of the system is the VAI state (as determined by monitoring the state bus 64), and therefore that the AEI has timed-out without any cardiac activity having been sensed. Hence, an A-pulse trigger signal is generated and sent to the A-pulse generator 18, so that the atrium can be stimulated. At the same time, an appropriate logic signal(s) is sent to the state logic 62 over the signal line(s) 80 to alert the state logic to the fact that the timer 76 has timed-out.

The state logic 62, in response to receiving the signal(s) from the time-out decode logic 78, and also in response to the current VAI state, triggers the next state of the prescribed sequence. For DDD operation, this state is typically a blanking state, or BLANK state, during which the P and R sense amplifiers, 22 and 24, are disabled. Accordingly, the state logic generates appropriate signal(s) on signal lines 36 and 38 to blank the P-wave sense amplifier 22 and the R-wave sense amplifier 24, and also causes the state registers 60 to change to a BLANK state, which state could be defined, for example, by the flip flops of the state registers 62 assuming a "0001" (hex "1") condition. This BLANK state, detected on the state bus 64, causes the memory control circuitry to retrieve an appropriate data word from memory that defines the length of the blanking interval, which data word is loaded into the programmable timer 76. As soon as the timer 76 times out, indicating that the prescribed blanking interval has elapsed, a time-out signal is generated that is sent to the time-out decode logic 78. Upon receipt of this time-out signal, and in response to the current state being a BLANK state, the time-out decode logic 78 sends an appropriate logic signal to the state logic 62. The state logic 62 responds by steering the state registers 62 to assume the next state in the prescribed sequence, which may be, for example, an AV-Interval state.

It is the AV-Interval state that has particular applicability to the present invention, because it is the duration of this state that the invention changes in order to avoid fusion. At the beginning of the AV-Interval state, another value is loaded into the programmable timer 76 that defines the length of the pacemaker-defined AV interval, or "AVI". This AVI value, in accordance with the invention, may change from cardiac cycle to cardiac cycle, or from another prescribed time interval (such as a plurality of cardiac cycles) to another prescribed time interval. If the timer 76 times-out without being reset, indicating that no R-wave has been sensed, the decode logic generates a V-pulse trigger signal, and notifies the state logic 62 of this event. The state logic, in turn, causes the next appropriate state to be entered, which state may be another blanking state, or BLANK state, similar to the one described above, but having perhaps a different duration. At the conclusion or timing out of this second BLANK state, the next state in the prescribed sequence is initiated, which state may be a refractory (REF) state.

If the timer 76 (while containing the AVI value) does not time-out before an R-wave in sensed, then the content of the timer at the time the R-wave occurs is representative of the AR interval sensed by the pacemaker. Such AR interval represents the natural conduction time of the heart to which the pacemaker is coupled, i.e., it represents the time from atrial activity to the occurrence of a natural ventricular depolarization. This AR interval value, in accordance with the present invention, may thus be used to steer the adjustment of the AV interval for use in the next cardiac cycle.

In general, the present invention contemplates two modes of AV adjustment. In a first mode, the AV interval is always set to be just a little bit longer than the natural conduction time of the patient's heart, i.e., just a little bit longer than the AR interval, so that the patient's heart is afforded as much opportunity as possible to beat on its own without applying a ventricular stimulus (V-pulse). In a second mode, the AV interval is always set to be just a little bit shorter than the natural conduction time of the patient's heart, i.e., just a little bit shorter than the AR interval, thereby assuring that a V-pulse is most always provided. Such second mode is particularly well suited for patient's suffering from a cardiomyopathy because the applied V-pulse significantly improves the patient's cardiac output. In either mode, it is important that the AV interval be set to a value that is different than the AR interval value so as to avoid fusion. Thus, depending upon the selected mode, the AV adjustment operation of the present invention uses the most recent AR interval value held in the timer 76, or equivalent timer, to guide the selection of the next AV interval value to be loaded in the timer 76 during the next (or a subsequent) cardiac cycle.

In the manner described above, the control system 26 assumes one state after another, thereby controlling the operation of the pacemaker. In general, a state is changed when the timer 76 times-out, or when a prescribed event occurs. Further, in accordance with the present invention, if a prescribed event occurs, e.g., the occurrence of a P-wave, then the next state may be a PV-Interval state. The PV-Interval state is the same as the AV-Interval state, described above, except that a different value is loaded into the programmable timer 76, which different value defines the length of the PV interval, or "PVI". As stated above, for the descriptions presented herein, reference is generally only made to the AV-interval state, but it is to be understood that such state may be, in fact, a PV-interval state if the atrial event that starts the state is a P-wave as opposed to an A-pulse.

It is noted that the state of the control system could also be changed by receipt of an appropriate command from the telemetry system.

The control system 26 of FIG. 2 may be realized using dedicated hardware circuits, or by using a combination of hardware and software (or firmware) circuits. The appropriate sequence of states for a given mode of operation, such as DDD or VDI, for example, can be defined by appropriate control of the memory control 74 and the state logic 62. These circuit elements, in turn, are most easily controlled through an appropriate software or firmware program that is placed or programmed into the pacemaker memory circuits. The manner of accomplishing such programming is known in the art.

A detailed description of the various circuits of the control system 26 of FIG. 2 will not be presented herein because all such circuits may be conventional, or may be patterned after known circuits available in the art. Reference is made, for example, to U.S. Pat. No. 4,712,555 wherein a state-machine type of operation for a pacemaker is described; U.S. Pat. No. 4,788,980, wherein the various timing intervals used within the pacemaker and their inter-relationship are more thoroughly described; and U.S. Pat. No. 4,944,298 wherein an atrial-rate based programmable pacemaker is described, including a thorough description of the operation of the state logic used to control such a pacemaker. The '555, '980 and '298 patents are incorporated herein by reference. It is noted that portions of one embodiment of the control system 26 that specifically relate to AV adjustment features of the present invention are further described below in conjunction with FIGS. 6 and 7.

Turning next to FIG. 3, the manner in which the AV interval is adjusted by the present invention in order to avoid fusion is illustrated. Shown in FIG. 3 is an "event line" 90 that depicts the cardiac events that may occur during a cardiac cycle. Such events are depicted by way of pulses, e.g., A-pulses 92, 93, or depolarization signals, e.g., an R-wave 94, or repolarization signals, e.g, a T-wave 96 (representing the repolarization of the ventricles), and thus are shown in a manner similar to how such events might appear in an intracardiac electrogram (EGM) signal, or a skin electrocardiographic (ECG) signal. However, for purposes of the present invention, it should be noted that the event line 90 is not intended to be an accurate representation of either an EGM or an ECG signal; rather, it is intended simply to diagrammatically depict the events that occur in a given cardiac cycle.

Note from FIG. 3 that the "cardiac cycle" comprises the time interval from atrial activity to the next atrial activity, e.g., from A-pulse 92 to the next A-pulse 93. The cardiac cycle may just as easily comprise, or be measured as, the time interval between ventricular activity and the next ventricular activity, e.g., from R-wave 94 to the next R-wave (or V-pulse) that occurs in the event line 90. However, such next R-wave (or V-pulse) is not shown in the event line 90 of FIG. 3, so the cardiac cycle is shown as the time between the A-pulses 92 and 93.

As seen in FIG. 3, the AR interval is shown as the time interval in the cardiac cycle following atrial activity (the A-pulse 92 for the condition shown in FIG. 3) to the occurrence of natural ventricular depolarization (the R-wave 94). Such AR interval thus represents the natural conduction time of the heart, i.e., the time it takes an atrial stimulus to travel to the ventricles through the atrioventricular (AV) node and the atrioventricular (AV) bundle. In order to avoid fusion, it is necessary that the AV interval of the pacemaker be set to a value different than the natural conduction time, or AR interval. The present invention accomplishes this by either starting with an AV interval that is shorter than the AR interval and gradually increasing the AV interval until it exceeds the AR interval, or starting with an AV interval that is longer than the AR interval and gradually decreasing the AV interval until it is less than the AR interval.

Thus, in a first adjustment mode contemplated by the present invention, the end goal is to have the AV interval longer than the AR interval, but not too much longer, so that the heart is afforded every opportunity to depolarize on its own without the necessity of a V-pulse. The reason that the AV interval should not be too much longer than the AR interval is because the natural conduction time (AR interval) will change somewhat to meet the physiological needs of the patient, and it is desirable to provide the V-pulse at a time in the cardiac cycle that tracks such needs. Thus, in accordance with such first adjustment mode, the AV interval is initially set to a very short value, and incrementally increased, at prescribed intervals, e.g., every cardiac cycle, until it crosses over the AR interval. The cross-over point is detected by monitoring the ventricular channel for the occurrence of an R-wave during each prescribed interval. That is, during the AV interval adjustment sequence, the AV interval is first set to a value much shorter than the AR interval, thereby assuring the generation of a V-pulse as the ventricular activity in the cardiac cycle. As the AV interval is increased, the V-pulse will continue to be generated for so long as the AV interval remains less than the AR interval. As soon as the AV interval becomes longer than the AR interval, an R-wave occurs, and the generation of the V-pulse is inhibited. Thus, for an AV interval that starts at a short value and is gradually increasing, the cross-over point is detected when an R-wave first occurs.

In a second adjustment mode contemplated by the present invention, the end goal is to have the AV interval shorter than the AR interval, but not too much shorter, so that a V-pulse is always provided during the cardiac cycle. Such mode is particularly adapted for patients suffering from a cardiomyopathy, as described in Applicant's copending patent application, previously referenced. Thus, in accordance with such second adjustment mode, the AV interval is initially set to a very long value, forcing R-waves to occur, and incrementally decreased, at prescribed intervals, e.g., every cardiac cycle, until it crosses over the AR interval. The cross-over point is detected when R-waves first cease to occur.

The AV interval will be approximately the same as the AR interval at the cross-over point, although there will normally be some difference between the two values as a function of how much the AV interval changes during each step of an adjustment cycle. Thus fusion will normally be avoided by simply using the AV interval value at the cross-over point. To further assure that fusion is avoided, however, the present invention typically adds on appropriate AV margin to the AV interval determined at the cross-over point.

The process of adjusting the AV interval in accordance with the first AV interval adjustment mode is further illustrated in FIG. 4. FIG. 4 is a graph of the AV interval value (vertical axis) verses elapsed time (horizontal axis). The units of time used on the horizontal axis are cardiac cycles; although it should be understood that this is only exemplary. Any other measure of elapsed time could be used, such as seconds or minutes. The heavy line 100 in FIG. 4 represents the natural conduction time of the patient, or the AR interval. This natural conduction time varies somewhat over time as the medical condition or physiological needs of the patient change. (It should be noted, as stated above in the background portion of the application, that the "conduction time" of a typical patient is not the parameter that changes most to alter the patient's heart rate. Rather, it is the rate of the stimulus from the SA node that sets the heart rate of the patient, and the rate of the stimulus from the SA node, in turn, affects the time between ventricular activity and subsequent atrial activity. Nonetheless, there are some changes that occur in the conduction time that vary over time, and that vary from patient to patient. The changes in the conduction time, or AR interval shown by the line 100 in FIG. 4, represent such changes.)

The pacemaker-defined AV interval is represented in FIG. 4 by the line 102. As seen in FIG. 4, this AV interval 102 is initially (as shown at the left-most edge in FIG. 4) greater than the conduction time interval 100. This is the desired relationship between the AV interval and the AR interval when the pacemaker is operating in the first adjustment mode. However, at regular intervals, e.g., at the end of a search time $T_s$, the pacemaker determines that a search should be started for a new AV interval value. Thus, at a time 104, a new AV search is started, which new search begins an AV interval adjustment sequence that eventually concludes with a new AV interval having been set.

The AV interval adjustment search sequence starts by immediately changing the value of the AV interval from its existing value, i.e., the AV value prior to the search time 104, to an initial search value. The initial search value will be a value that is deliberately set to be less than the AR interval. In FIG. 4, the initial value is selected to be the minimum AV interval value, $AV_{MIN}$. It is to be understood, however, that using $AV_{MIN}$ as the initial search value is only exemplary. For example, the pacemaker logic may have selection logic incorporated therein that keeps track of the most recent value of the AR interval. The initial search value for the AV interval could then be set to a value that is a prescribed amount less than such most recent AR interval value.

In any event, once the initial AV interval search value has been set, such value is used as the AV interval value for a prescribed adjustment time period, which prescribed adjustment time period includes at least one cardiac cycle. For the adjustment sequence shown in FIG. 4, the adjustment time period comprises one cardiac cycle, but it is to be noted that the adjustment time period could just as easily comprises two or three or more cardiac cycles. During the cardiac cycle, the ventricular channel activity is monitored to determine if an R-wave (evidencing natural conduction) or a V-pulse (evidencing the expiration of the AV interval prior to natural conduction) occurs. A V-pulse is generated for the first step of the adjustment sequence because the AV interval at that point in the sequence is much shorter than the natural conduction time, or AR interval.

After the initial AV interval search value has been used for the prescribed adjustment sequence, the AV interval value is increased by a prescribed amount, $AV_s$, for the next adjustment time period. Again, a determination is made to determine the type of ventricular channel activity (V-pulse or R-wave) that occurs during the adjustment time period. This process continues, with the AV interval value being increased for each succeeding adjustment time period, in stairstep fashion from the initial AV interval search value until the AV interval value, represented by the line 102, crosses over the natural conduction time value, represented by the bold line 100. The first cross-over point that occurs during this stair-step adjustment sequence for the situation shown in FIG. 4 is at 106. That is, at the time 106, conduction starts, and an R-wave occurs.

Once the cross-over point has been identified in the adjustment sequence, the AV interval value used for the most recent adjustment time period represents an AV interval value that meets the desired adjustment goal: i.e., an AV interval value that is greater than, but close to, the natural conduction time. Such AV interval value is shown at 108 in FIG. 4. However, to ensure that there is an adequate operating margin that maintains this desired goal, the present invention adds an AV margin, $AV_M$, to the AV interval value at the cross-over point, resulting in a final AV interval value for the adjustment sequence, one adjustment time period later, as shown at 110.

After the value of the AV interval has been set in a given adjustment sequence, as described above, the final AV interval value is used by the pacemaker until one of two possible events occur that trigger a new AV interval adjustment sequence. A first adjustment-sequence-triggering event, for the first mode AV adjustment shown in FIG. 4, is for natural A-V conduction to stop. When A-V conduction stops, that means the conduction time interval, or AR interval, has changed so that it is no longer less than the AV interval. Such condition occurs in FIG. 4 at 112. Thus, in accordance with the particular application of the present invention shown in FIG. 4, the generation of a V-pulse in a given cardiac cycle when the immediately preceding cardiac cycles all included R-waves instead of V-pulses, triggers a new AV interval adjustment sequence, which sequence begins at 114. The adjustment sequence proceeds as previously described, with the AV interval value being shortened to an initial starting value, and then increasing in stair-step fashion in order to identify the crossover point, which cross-over point is shown at 116 in FIG. 4. The AV margin, $AV_M$, is then added to the cross-over value of the AV interval, resulting in the final AV interval value, as shown as 118.

It is noted that for some patients, and in some embodiments of the present invention, it may be desirable to make the first AV adjustment sequence triggering event be the occurrence of a prescribed number of R-waves within a prescribed number of cardiac cycles, e.g., at least two R-waves in three cardiac cycles; or at least five R-waves in seven cardiac cycles, so as to preclude the possibility that an abnormal single heart beat might trigger an AV interval adjustment sequence when, in fact, the conditions for needing an AV interval adjustment sequence, are not present.

The second event that triggers an AV interval adjustment sequence in accordance with the present invention is the expiration of a search interval $T_S$. The search interval $T_S$ starts as soon as the cross-over point has been reached in a given adjustment sequence. Thus, as shown in FIG. 4, the $T_S$ interval begins for example at time 116. (If desired, the interval could just as well begin at the next adjustment time period after the AV margin has been added.) A $T_S$ counter is used to keep track of the search time, i.e., to determine if the $T_S$ interval has expired. The $T_S$ counter is reset at the beginning of a given search sequence, e.g., at times 104 and 114 in FIG. 4. In FIG. 4, the next AV interval adjustment sequence begins at time 120, at the expiration of the $T_S$ interval. The situation shown in FIG. 4 assumes that between the time 118 and the time 120, something has happened to the patient that significantly lowered the natural conduction time. For example, the patient may have experienced physical exercise, which would tend to temporarily lower or shorten the conduction time, or AR interval. In any event, at the expiration of the $T_S$ interval, at time 120, another adjustment search sequence is started. This search sequence proceeds as described above, except that the cross-over point 122 is reached much sooner in the adjustment sequence than before due to the lowering of the natural conduction time, or AR interval. The final value of the AR interval is determined, as before, as the AV interval value at the cross-over point 122, plus the margin value, $AV_M$.

Continuing with the description shown in FIG. 4, because the AR interval (conduction time) is gradually increasing after the cross over at point 122, it isn't long before the AR interval exceeds the newly set AV interval value, triggering another search sequence at time 124. Such other search sequence proceeds as previously described, eventually setting a new AV interval value at 126.

One feature of the AV interval adjustment sequence of the present invention not invoked for the situation shown in FIG. 4, but which feature applies to the first mode searches performed in FIG. 4 (as well as to the second mode adjustment searches illustrated in FIG. 5) is that the control system logic monitors the time interval between AV interval adjustment sequences, $t_A$. If $t_A$ is less than a first prescribed threshold, indicating that the AV interval search sequences are being invoked more often than is desired, then the invention automatically increases the AV margin, $AV_M$, in order to reduce the frequency of triggering the AV search sequences. Conversely, if $t_A$ exceeds a second prescribed threshold, indicating that the AV interval search sequence has not been invoked for a long time, then the AV margin, $AV_M$, is reduced back to its original value, which value is preferably a programmed value, but could also be a fixed value or an adaptive value (e.g., being a certain percentage of the AV interval value).

The process of adjusting the AV interval in accordance with the second AV interval adjustment mode is further illustrated in FIG. 5. It will be noted that FIG. 5 is substantially the same as FIG. 4, with the AV interval value being represented by line 102, and the AR interval (natural conduction time) being represented by the bold line 100. However, in FIG. 5, the AV adjustment sequence adjusts the AV interval in the opposite direction from that shown in FIG. 4. Thus, when a new search is started, at time 130, the AV interval value is set to an initial adjustment sequence value 131 that is much longer than the AR interval. For the condition shown in FIG. 5, the initial AV search value is set to the maximum AV interval value 131, $AV_{MAX}$, although this is only exemplary. The AV interval value is then maintained for the prescribed adjustment time period (which adjustment time period for the situation shown in FIG. 5 is one cardiac cycle, but could be any number of cardiac cycles or time period) and is then reduced by a prescribed amount, $AV_S$, to a next value for use during the next adjustment time period. The adjustment of the AV interval continues in this stair-step fashion until the cross-over point 132 is identified. The cross-over point, for the adjustment mode shown in FIG. 5, occurs when an R-wave ceases to be detected during the adjustment time period. Once the cross-over point is located, the AV interval value used during the most recent cardiac cycle (the cycle during which the cross-over was noted) is then at a value that meets the goals of the adjustment sequence: an AV interval value that is less than, but close to, the AR interval value. To ensure an added degree of margin in meeting this goal, the invention subtracts an AV margin, $AV_M$, from the AV interval value used when cross-over was detected in order to arrive at a final AV interval value 134.

The adjustment process illustrated in FIG. 5 continues, as described above with an AV adjustment sequence being triggered whenever the natural conduction time becomes less than the AV interval, as occurs at time 136, or whenever the search time interval, $T_S$, times-out, as occurs at time 140.

FIG. 5 also illustrates the adjustment of the AV margin, $AV_M$, in the event that a second AV interval adjustment search commences within a time $t_A$ of a prior search that is less than a prescribed threshold. In such instance, as shown in FIG. 5, at the conclusion of the second search, the margin is increased to a value $AV_M'$, which value may be, e.g., twice as large as $AV_M$.

The search time $T_S$ used by the present invention is used so that not too much time goes by without adjusting the AV interval. Otherwise, the natural conduction time could change in a direction that leaves a large difference between it and the AV interval without such difference being detected. The search time $T_S$, however, is preferably not too short of a time period, else AV interval adjustments might occur too frequently. A typical minimum value for $T_S$ is 30-60 minutes. A typical maximum value for $T_S$ is 48-72 hours.

The threshold used in connection with monitoring the time between adjustment search sequences, $t_A$, is typically measured in cardiac cycles, and will usually range from 10-30 cardiac cycles. Such threshold is preferably a programmable number, but it may also be a fixed number, or an adaptive number (computed, e.g, as a prescribed percentage or ratio of previously measured $t_A$ time periods).

In addition to the search time $T_S$ and the monitoring of the elapsed time $t_A$ in between adjustment searches, the present invention also utilizes a suspend search time T1 that may be invoked in the event that a prescribed number of searches occur within a relatively short time period. Such suspend search time thus recognizes that it may not be in the patient's best interest to have adjustment searches being performed again and again and again. The repeated need to perform a search, as determined by the parameters monitored by the invention, may actually be symptomatic of additional problems that need to be investigated by a physician. Hence, in such instances—where the search sequence has been invoked more than, e.g., a dozen times within a 30-minute period—the invention automatically suspends searching for a time period T1. The time period T1 is a programmable value that is typically measured in terms of days, e.g., 3 days. Thus, if AV interval searching is suspended, then during the T1 time period, the pacemaker continues to perform its programmed pacing function, as always, but without making any adjustments to the AV interval value.

Turning next to FIG. 6, a functional block diagram is illustrated of the pacemaker components used to carry out the AV interval adjustment sequences shown in FIGS. 4 and 5. It is noted that most of the components shown in FIG. 6 are included in the control system 26 or memory 40 (FIG. 1), and more particularly are considered part of the state logic 62, programmable timer 76, and/or T.O. Decode Logic 78 (FIG. 2). It is noted that the function performed by the components shown in FIG. 6 can be achieved using numerous hardware and/or microprocessor-based configurations. That which is shown in FIG. 6 is merely exemplary of one such configuration.

As seen in FIG. 6, the memory 40 includes addressable locations therein that contain various data and parameters used during operation of the pacemaker. One set of such parameters are the various AV interval values, $AV_{MIN}$, AV1, AV2, . . . AVn, $AV_{MAX}$ that may be used during the AV adjustment sequence. Such set of values are then retrieved, one at a time during a given adjustment time period, and loaded into an AV register 160 and an AV timer 162. The AV timer 162 is used to define the AV interval by loading the desired AV interval value therein and counting down to zero, issuing an appropriate time-out (T.O.) signal when the countdown has been completed. Alternatively, in the event an R-wave occurs before the AV interval has timed-out, the count remaining in the AV timer 162 provides a measure of the AR interval, or conduction time. The initial value of the AV interval, loaded in the register 160, may then be compared to the AR interval in order to ascertain the difference between the two values. Such difference may be used to steer the selection of the next AV value, thereby providing a truly adaptive adjustment of the AV interval.

Operation of the AV register 160 and the AV timer 162 is controlled by the AV adjustment logic 164. Basically, included in such logic is a means for detecting the occurrence of atrial activity. Such means are functionally represented in FIG. 6 by the OR gate and the A-V latch 168. The occurrence of either a P-wave, represented by the signal "IPW", or the occurrence of an "A-Trig" signal (used to trigger the A-PG 18 in FIG. 1 to generate an A-pulse) are sensed by the OR gate 166, with either event causing the A-V latch to be set. Similarly, the occurrence of either an R-wave, represented by the signal "IRW", or the occurrence of a "V-Trig" signal (used to trigger the V-PG 20 in FIG. 1 to generate a V-pulse) are sensed by OR gate 170 to reset the A-V latch 168. Thus, during the AV interval portion of a cardiac cycle, the A-V latch 168 is set, and during the V-A interval portion of a cardiac cycle, the A-V latch 168 is reset.

The output of the OR gate 170 also serves as a cardiac cycle clock signal, which cycle clock signal is counted in a cycle counter 172. Such cycle counter 172 is used to define the search time $T_S$, as well as to check the time that elapses between AV adjustment sequences, $t_A$. The cycle clock signal is further used to clock a two-bit register 174 that monitors the type of ventricular activity (V-pulse or R-wave) that occurred during the last two cardiac cycles. If the current cardiac cycle contains an R-wave, as indicated by the IPW signal, then such signal sets the first bit to a "1". If the current cardiac cycle contains a V-pulse, as indicated by the V-Trig signal, then such signal sets the first bit to a "0". At the occurrence of the next cardiac cycle, this bit is shifted to the second bit of the register, and the first bit is set appropriately to indicate the type of ventricular activity in the new current cardiac cycle. Thus, in this manner, the register 174 always contains an indication of the type of ventricular activity that occurred during the two most recent cardiac cycles.

An Exclusive OR gate 176 checks the contents of the register 174 to detect if a change has occurred. If the present cardiac cycle includes an R-wave, whereas the cardiac cycle immediately preceding the present cardiac cycle contained a V-pulse, then the output of the Exclusive OR gate 176 will be a "1", indicating that a change occurred in the type of ventricular activity. Similarly, if the present cardiac cycle includes a V-pulse, whereas the cardiac cycle immediately preceding the present cardiac cycle contained an R-wave, then the output of the Exclusive OR gate 176 will also be a "1", indicating that a change occurred in the type of ventricular activity. However, if the two most recent cardiac cycles both contained a V-pulse, or both contained an R-wave, then the output of the Exclusive OR gate 176 will be a "0", indicating that no change occurred in the type of ventricular activity over the last two cardiac cycles.

Logic circuitry 178 within the AV adjustment logic 164 monitors the A-V Latch 168 (represented by an Activity signal), the cycle counter 172, and the Exclusive OR gate 176 (represented by a V-Channel change signal), in conjunction with the contents of the AV timer 162 and the AV register 160, in order to carry out the AV adjustment sequences described above.

Figure 7:
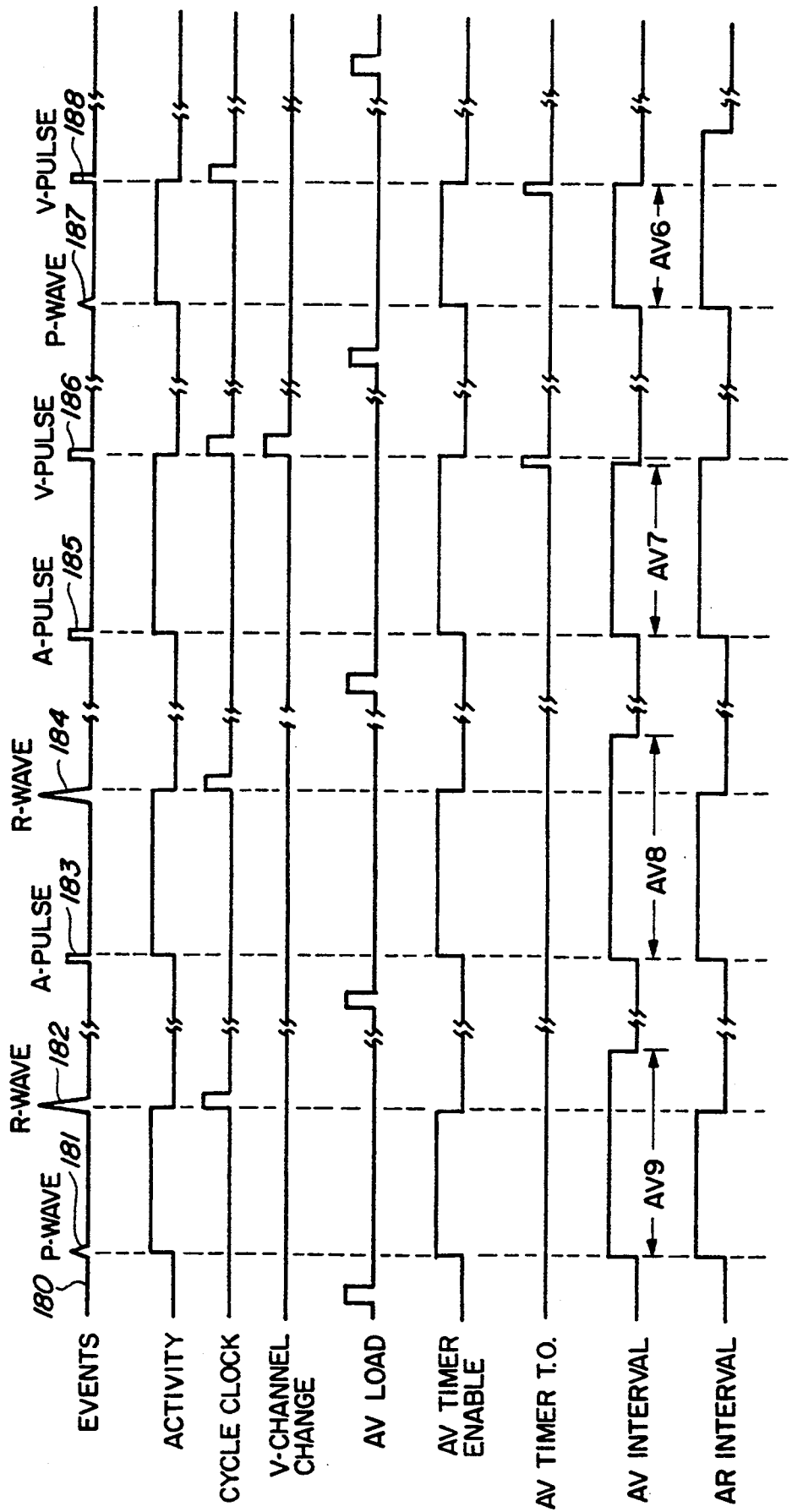
FIG. 7 is a timing diagram that illustrates some of the signals associated with the operation of the circuitry of FIG. 6.

The above process is further illustrated with reference to FIG. 7, which shows a timing waveform diagram associated with the operation of the circuitry of FIG. 6. As seen in FIG. 7, various events are represented in the event line 180 at the top of the figure. These events include, in the following order, a P-wave 181, an R-wave 182, an A-pulse 183, an R-wave 184, an A-pulse 185, a V-pulse 186, a P-wave 187, and a V-pulse 188. As a result of the occurrence of these signals, the Activity signal, which is the output of the A-V latch 168, is set to a high (or "1" value) following the occurrence of atrial activity, and is set to a low (or "0" value) following the occurrence of ventricular activity. The occurrence of ventricular activity also generates a cycle clock signal, with one pulse for each cardiac cycle. The V-Channel Change signal remains at a low or "0" value except upon the occurrence of the V-pulse 186, which V-pulse occurs in the cardiac cycle following the R-wave 184.

The AV Load signal shown in FIG. 7 is generated by the logic circuitry 178 during the cardiac cycle to load a desired AV interval value into the AV register 160 and the AV timer 162. Note that such loading occurs prior to the beginning of the AV interval, so that the associated registers and timers are loaded and ready to go upon the occurrence of atrial activity. Thus, as soon as atrial activity occurs, the AV timer is enabled, as controlled by the AV Timer Enable signal. The AV Timer Enable signal allows the AV timer 162 to continue counting until ventricular activity occurs. If the ventricular activity is a V-pulse, then the AV timer has timed-out, and a Time-Out pulse is generated, as shown by the AV Timer T.O. signal line in FIG. 7. If the ventricular activity is an R-wave, then the AV timer has not timed-out, but still contains a count therein representative of the AR interval. Note that the AV Timer Enable signal is thus essentially the same as the Activity signal.

The bottom two signal lines in FIG. 7 show, in diagrammatic form, the desired AV interval and the AR interval, assuming an adjustment of the AV interval from a value AV9 to a value AV6, where the AV values are getting shorter, and assuming a second mode AV adjustment is being performed (as in FIG. 5). Note that the first AV value, AV9, is significantly longer than the AR interval, and hence the R-wave 182 is generated, inhibiting the generation of any V-pulse. Based on the difference between AV9 and the corresponding AR interval, a new AV interval, AV8 is selected. This new value of AV8 may simply be the next value of the AV interval stored in memory; may be the value AV9 reduced by a prescribed step size, $AV_S$; or may be an adaptive value that is computed based on the difference between AV9 and its corresponding AR interval. In any event, as seen in FIG. 7, the next AV interval value, AV8, is also still longer than the corresponding AR interval. Hence, the R-wave 184 occurs, and the generation of a V-pulse is inhibited. The next AV value, AV7, is just slightly shorter than the corresponding AR interval. Hence, the V-pulse 186 is generated before the R wave occurs. As the V-pulse 186 is very near to the end of the natural conduction time, as evidenced by the AR interval being just slightly longer than the AV7 interval, it is desirable to further decrease the AV interval, as indicated by the AV interval AV6 that is loaded for use during the next cardiac cycle. The AV6 value is the AV7 value adjusted by the appropriate AV margin, $AV_M$.

It is noted that the AV register 160 is only needed when an adaptive adjustment of the existing AV interval is to be made as a function of the difference between the existing AV interval and the AR interval, or as a computation using a prescribed step size, $AV_S$. The register 160 thus provides a baseline reference of what the AV interval was at the start of the cardiac cycle, and provides a convenient holding location to temporarily hold the current AV value during the cardiac cycle so that the next AV value can be easily computed therefrom for the next cardiac cycle, or other adjustment period.

Turning next to FIGS. 8-1 and 8-2, a flowchart is shown that further details the manner in which the present invention carries out the AV adjustment sequence illustrated in FIGS. 3-5. It should be kept in mind that the primary object of this AV interval adjustment is to automatically set an AV interval value that is near, but different than, the natural conduction time interval. In a first adjustment mode, the AV interval is set to be just greater than the natural conduction time, or AR interval, thereby favoring the occurrence of R-waves. In a second adjustment mode, the AV interval is set to be just less than the natural conduction time, or AR interval, thereby favoring the generation of V-pulses. In the flowchart of FIGS. 8-1 and 8-2, each main step of the sequence is shown as a "block" or "box", with each block having a reference numeral assigned thereto to aid in the explanation of the sequence. Such flowchart is particularly helpful when the invention is implemented using a microprocessor, or equivalent processing device, that follows a stored program, with the flowchart representing the stored program that is used by such processor.

As shown in FIG. 8-1, after starting or enabling the automatic AV interval adjustment feature, (block 200), the operating values associated with the using such automatic adjustment feature are set (block 202). Such values include, e.g., the minimum and maximum values for the AV interval, $AV_{MIN}$ and $AV_{MAX}$; the search time $T_S$; the suspend search time T1; the initial AV margin, $AV_M$, an AFLAG (indicating whether the first or second adjustment mode is to be used), and the like. Then, a T1 timer is reset (block 204) Once the T1 timer is reset, all of the initial conditions are set, and the AV adjustment process is ready to begin at point "A" in the flowchart.

A first step in the adjustment process is to determine if the T1 (suspend) timer has expired (block 206). Obviously, if the process has just started, then there has not yet been an occasion to suspend further searching. But, if the process has been going on for some time, and if the suspend function has been invoked, then the adjustment sequence will not be invoked or started until T1 has expired. If the T1 (suspend) timer has not expired, then normal pacing is performed (block 208) without any adjustments being made to the AV interval. Periodically, or as programmed, a determination is made as to whether pacing should continue with the automatic AV interval adjustment feature enabled (block 210). If not, then the automatic adjustment feature is disabled and the adjustment process stops (block 212).

Once the suspend time has elapsed (block 206), then a determination is made as to whether the first or second adjustment mode is to be followed. Such determination is made by examining the AFLAG (block 214). If AFLAG is a "0", for example, then that means that the second adjustment mode is to be used wherein the AV interval is to be set to a value less than the natural conduction time, AR, as illustrated in FIG. 5. In which case, the flowchart continues, through connector "B", to FIG. 8-2. If AFLAG is a "1", then that means that the first adjustment mode is to be used wherein the AV interval is set to a value greater than the natural conduction time, AR, as illustrated in FIG. 4.

To begin the first adjustment mode, as seen in FIG. 8-1 beginning at connector "C", the $T_S$ counter is first reset and a flag, RFLAG is reset (block 216). As indicated below, RFLAG is used to indicate when cross-over occurs. Next, to start the adjustment sequence, the AV interval is set to its initial adjustment value (block 218). The AV interval then begins during the next cardiac cycle (block 220), and a determination is made as to whether an R-wave is sensed during the timing out of the AV interval (blocks 222, 224). Normally, during the first pass through the adjustment sequence, with the new AV interval set to is initial value, an R-wave will not be sensed. Hence, the AV interval times-out (block 222) without the sensing of an R-wave (block 224). Then, a determination is made as to whether the RFLAG has been set (block 236). In this instance, for the first time through the sequence, no R-waves have yet been detected, so the RFLAG is not set. Thus, a V-pulse is issued (block 240). After the V-pulse is issued, the AV interval value is increased by a specified amount, which may be a fixed step size $AV_S$. With a new AV interval in place, the process repeats during the next adjustment time period (which is usually the next cardiac cycle), with the AV interval starting (block 220), a determination being made as to whether an R-wave occurs during the AV interval (blocks 222, 224), a V-pulse being issued (block 240), and the AV interval being increased to its next adjustment value (block 242).

The above process continues to repeat as many times as is necessary, with each pass through the sequence utilizing a different AV value, until an R-wave is detected before the AV interval times-out (blocks 222, 224). When an R-wave is sensed during the AV interval (block 224), then the RFLAG is set (block 224). The RFLAG is used as a means of keeping track of when the first R-wave occurs, and hence when cross-over occurs. After setting the RFLAG, a determination is made as to whether the search time counter $T_S$ is zero (block 228). Because as the $T_S$ counter is reset to zero at the beginning of the adjustment sequence (block 216), and because the incrementing of the $T_S$ counter has not yet started, this determination is made simply to determine if the present pass through this portion of the sequence is the first pass of the adjustment sequence through this portion of the sequence. If so, i.e., if $T_S=0$, then the current AV interval value is the cross-over AV value, which value may be increased by the AV margin value, $AV_M$ (block 230). Then, the $T_S$ counter is incremented (block 232), and a determination is made as to whether the $T_S$ counter has reached its terminal count (block 234). If not, then the cycle repeats by starting the AV interval (block 220), using the final AV value set by the adjustment sequence (obtained by adding the AV margin to the cross-over AV value, at block 230).

With the final AV value being used, an R-wave should normally be sensed during the time-out of the AV interval (blocks 222, 224) because the AV value was deliberately set to a value greater than the natural conduction time, the AR interval. Thus, each time through the loop, i.e., during each cycle, the $T_S$ counter will be incremented (block 232), and a determination will be made if the $T_S$ counter has reached its terminal count.

The above cycling through the sequence loop (blocks 220, 224, 228, 232 and 234) continues until one of two events transpire. The first event that causes the sequencing to stop is the failure of an R-wave to occur during the timing out of the AV interval (block 222). If no R-wave is sensed, and if the RFLAG is set (block 236), and if additional searching is not to be suspended (block 244), then a new search sequence begins by jumping back to point "C" on the flowchart. As discussed above, searching (i.e., performing an adjustment of the AV interval by searching for a new AV interval value that is near, but not the same as, the conduction time interval) may be suspended if too many searches have been performed in a short time period. Should searching be suspended, then the T1 timer is started, and the process reverts back to point "A" on the flowchart.

The second event that causes the sequencing (blocks 220, 224, 228, 232 and 234) to stop is the timing out of the $T_S$ counter (block 234). If the time period defined by the $T_S$ counter has expired, then a determination is made as to whether searching should be suspended (block 244), and if not, the next search is immediately started by having the sequence revert back to point "C" on the flowchart. If searching is to be suspended, then the T1 timer is started, and the process reverts back to point "A" on the flowchart.

Turning next to FIG. 8-2, the sequence that is followed when the second adjustment mode is to be used is illustrated (point "B" on the flowchart). This sequence closely parallels the sequence followed when the first adjustment mode is used, as described above. The sequence starts by resetting the $T_S$ counter and a VFLAG (block 250). The VFLAG, similar to the RFLAG, is used to indicate when cross-over first occurs, and the VFLAG is set, as explained below, when the first V-pulse occurs. After resetting the VFLAG and $T_S$ counter, the AV interval is set to its initial value for use in the adjustment search. For the second adjustment mode, the initial value is set to a value that will be longer than the conduction time, e.g., $AV_{MAX}$ (block 252). Then, during the pacing cycle, the AV interval is started (block 254), and a determination is made as to whether an R-wave occurs during the timing out of the AV interval (blocks 256, 258). During the first pass through the adjustment sequence, an R-wave should occur, because the AV interval starts out at a value known to be longer than the conduction time. If the VFLAG is not set (block 260), which it should not be at this part of the sequence, then the AV interval is decreased by a prescribed amount, e.g., a prescribed step size $AV_s$ (block 264). Then the sequence repeats (blocks 254, 258, 260, 264), with a different, shorter, value of the AV interval being used during each pass through the sequence until the cross-over point is reached.

The cross-over point is reached when the AV interval being used is less than the natural conduction time, causing the AV interval to time-out (block 256) without sensing an R-wave (block 258). When the AV interval times-out (block 256), the VFLAG is set (block 266), and a V-pulse is issued (block 268). If the $T_S$ counter is zero (block 270), which it will be during the first pass through this portion of the sequence, then the specified AV margin, $AV_M$ is subtracted from the cross-over AV value in order to arrive at the final AV adjustment value (block 272). A determination is then made as to whether the $T_S$ counter is at its terminal count (block 276), and if not, the sequence repeats (blocks 254, 256, 268, 270, 274, 276), continuing to use the final AV interval value, until one of two events occurs, which events will usually trigger a new search sequence.

The first event that can trigger a new search sequence after a final AV interval value has been set is the occurrence of an R-wave (block 258) before the timing out of the AV interval (block 256). When an R-wave is sensed, a determination is made as to whether the VFLAG is set (block 260). If it is set, then a new search sequence will be started unless searching is to be suspended (block 278). The new search for an AV interval value starts by returning to point "B" on the flowchart.

The second event that can trigger a new search sequence after a final AV interval value has been set is the timing out of the $T_S$ counter (block 276). Should the $T_S$ time period elapse, then a new search is started by returning to point "B" on the flowchart, absent a determination that all searching (adjustment of the AV interval) is to be suspended (block 278). If searching is to be suspended, then the T1 timer is started (block 280), and the sequence returns to point "A" on the flowchart (FIG. 8-1).

As described above, it is thus seen that the present invention provides an implantable pacemaker that automatically adjusts its AV interval to a value that is just less than, or just greater than, the natural conduction time of a patient's heart.

As further described above, it is seen that the invention provides such adjustment of the AV interval while avoiding fusion, i.e., the issuing of a V-pulse on top of an R-wave.

The invention also provides, as seen from the above description, an AV interval adjustment sequence, or technique, that quickly and automatically searches for the desired AV interval value—a value that is just less than or just greater than the natural condition time interval—and attaches a prescribed margin thereto, thereby assuring that the desired AV interval value is maintained while avoiding fusion. Additionally, it is seen that the prescribed margin may be adaptively changed, as required, in order to minimize the frequency at which the adjustment technique is invoked.

As also described above, it is seen that the invention provides an automatic AV interval adjustment procedure that is automatically invoked when needed, and that can be automatically suspended if invoked too often.

While the invention herein disclosed has been described by means of specific embodiments and applications thereof, numerous modifications and variations could be made thereto by those skilled in the art without departing from the scope of the invention set forth in the claims.

What is claimed is:

1. An implantable pacemaker comprising:
   atrial sensing means for sensing an atrial depolarization (P-wave);
   atrial pacing means for generating an atrial stimulation pulse (A-pulse);
   ventricular sensing means for sensing a ventricular depolarization (R-wave), and;
   ventricular pacing means for generating a ventricular stimulation pulse (V-pulse);
   means for storing operating instructions and control parameters; and
   controlling means coupled to said storing means, said atrial and ventricular sensing means and said atrial and ventricular pacing means for coordinating the operation of said atrial and ventricular sensing means, and said atrial and ventricular pacing means, in accordance with said operating instructions and said control parameters, said controlling means comprising:

first timing means for defining an AV interval;

second timing means for defining an atrial escape interval;

third timing means for measuring a conduction time interval, said conduction time interval comprising the time between atrial activity and sensing an R-wave, atrial activity comprising either of sensing a P-wave and generating an A-pulse;

first logic means for triggering said ventricular pacing means at the conclusion of said AV interval only in the event an R-wave is not sensed during said AV interval, said AV interval commencing with said atrial activity;

second logic means for triggering said atrial pacing means at the conclusion of said atrial escape interval only in the event a P-wave is not sensed during said atrial escape interval; and adjustment means for automatically adjusting said AV interval to a value that is different than said conduction time interval;

whereby V-pulses that are generated by said pacemaker are generated at a time that is different than said conduction time, thereby avoiding fusion between said V-pulses and said R-waves.

2. The implantable pacemaker, as set forth in claim 1, having an existing AV interval value, wherein said control parameters include parameters stored therein defining a maximum AV interval value, a minimum AV interval value, an adjustment time period value, an initial AV adjustment value, and an incremental difference value, and wherein said adjustment means further comprises:

first means for changing the value of said AV interval from said existing AV interval value to said initial AV adjustment value for said adjustment time period;

second means for changing the value of said AV interval in stair-step fashion, with said AV interval assuming a new AV interval value that differs from the preceding AV interval value by said incremental difference value for each of a plurality of subsequent adjustment time periods, said initial AV adjustment value and new AV interval values always being within the range defined by said maximum AV interval value and said minimum AV interval value;

means for determining if there is a change in the type of ventricular activity that occurred in the most recent adjustment time period compared to the type of ventricular activity that occurred in the adjustment time period just prior to the most recent adjustment time period; and means for setting a final AV adjustment value as a function of the AV interval value used in the most recent adjustment time period for which a change was detected in the type of ventricular activity that occurred.

3. The implantable pacemaker, as set forth in claim 2, wherein said pacemaker is programmably configurable to operate in at least a first mode and a second mode, said setting means further comprising:

first mode means setting said final AV adjustment value to a value that is greater than said conduction time interval by a specified amount, said first mode means active when said pacemaker is programmably configured to operate in said first mode, whereby an R-wave will normally occur before the termination of said AV interval; and second mode means setting said final AV adjustment value to a value that is less than said conduction time interval by a specified amount, said second mode means active when said pacemaker is programmably configured to operate in said second mode, whereby a V-pulse will normally be generated prior to occurrence of an R-wave.

4. The implantable pacemaker, as set forth in claim 3, wherein said initial AV adjustment value comprises said minimum AV interval value when said pacemaker is programmably configured to operate in said first mode; and comprises said maximum AV interval value when said pacemaker is programmably configured to operate in said second mode.

5. The implantable pacemaker, as set forth in claim 3, wherein said final AV adjustment value is set by said setting means to be the AV interval value used in the most recent adjustment time period for which a change was detected in the type of ventricular activity that occurred plus: (1) a positive AV margin for a pacemaker configured in said first mode, whereby the final AV adjustment value is longer than the AV interval value used in the most recent adjustment time period, and (2) a negative AV margin for a pacemaker configured in said second mode, whereby the final AV adjustment value is shorter than the AV interval value used in the most recent adjustment time period.

6. (amended) implantable pacemaker, as set forth in claim 5, wherein said AV margin comprises a multiple of said incremental difference value.

7. The implant able pacemaker, as set forth in claim 6, wherein said AV margin comprises one said incremental difference value.

8. The implantable pacemaker, as set forth in claim 2, wherein said adjustment means adjusts the AV interval value whenever each of the following occurs: (1) there is a change in the type of ventricular activity that occurs at a time when the AV interval value is not being adjusted, and (2) a search interval, $T_S$, times-out; said search interval, $T_S$, beginning upon the setting of said AV interval value to its initial AV adjustment value by said first changing means, and concluding a programmable search time interval thereafter.

9. The implantable pacemaker, as set forth in claim 8, wherein said search interval, $T_s$, comprises 1–72 hours.

10. The implantable pacemaker, as set forth in claim 2, wherein said adjustment means further comprises:

means for monitoring the time interval between successive changings by said first changing means of the AV interval value; and means for automatically changing the final AV adjustment value to increase the difference between it and the conduction time in the event the time interval between said successive changings is less than a prescribed threshold.

11. The implantable pacemaker, as set forth in claim 10, wherein said prescribed threshold comprises 10–30 cardiac cycles, where a cardiac cycle comprises the time interval between consecutive ventricular activity.

12. The implantable pacemaker, as set forth in claim 2, wherein said prescribed adjustment time period comprises at least one cardiac cycle, a cardiac cycle comprising the time interval between consecutive ventricular activity.

13. The implantable pacemaker, as set forth in claim 12, wherein the prescribed adjustment time period comprises one cardiac cycle.

14. An implantable dual-chamber pacemaker that automatically adjusts its AV interval and avoids fusion between the generation of a ventricular stimulation pulse (V-pulse), at the conclusion of said AV interval, and the occurrence of natural ventricular depolarization, as evidenced by the occurrence of an R-wave, said pacemaker comprising:

means for sensing atrial activity in an atrial channel;

means for sensing an R-wave and generating said V-pulse; and first control means for defining said AV interval as the longest time interval the pacemaker will allow from the occurrence of atrial activity until the generation of a V-pulse, the occurrence of an R-wave during said AV interval causing the generation of a V-pulse to be inhibited;

second control means for recognizing a need to adjust said AV interval from its present value to a new value;

third control means for adjusting said AV interval from its present value to an intermediate value, when an adjustment in the AV interval is needed, following a prescribed adjustment sequence;

forth control means for determining when in the adjustment sequence the AV interval crosses over an AR interval, said AR interval comprising the time interval between atrial activity and sensing an R-wave, and thereby representing a measure of the natural conduction time of a heart to which said pacemaker is coupled; and fifth control means for setting the new AV value of said pacemaker to a value that is a prescribed difference from said AR interval;

whereby a V-pulse and an R-wave will not occur at the same time, thereby avoiding fusion, even though the AV interval is automatically adjusted when needed.

15. The dual-chamber pacemaker, as set forth in claim 14, wherein said pacemaker further comprises a sixth control means for defining a programmable search interval, $T_S$, that begins upon the starting of said prescribed adjustment sequence, and wherein said control means begins said prescribed adjustment sequence whenever either one of two events occur; the first event comprising a change in the type of ventricular activity, i.e., an R-wave or a that occurs during a current cardiac cycle as compared to the type of ventricular activity that occurred during an immediately preceding cardiac cycle, where a cardiac cycle comprises the time interval between consecutive ventricular activity; the second event comprising the timing out of said search interval, $T_S$.

16. The dual-chamber pacemaker, as set forth in claim 15, wherein said programmable search interval comprises at least 30 minutes.

17. The dual-chamber pacemaker, as set forth in claim 15, wherein said prescribed adjustment sequence comprises a multi-step sequencing means, wherein said AV interval assumes a prescribed value during each step, and wherein each step lasts a prescribed time interval.

18. The dual-chamber pacemaker, as set forth in claim 17, wherein said multi-step sequencing means comprises a stair-step sequencing means wherein said AV interval assumes an initial starting value, and thereafter assumes in each step a succeeding value that is a prescribed difference from the AV interval value of the prior step.

19. The dual-chamber pacemaker, as set forth in claim 15, wherein said pacemaker further comprises a seventh control means for automatically increasing the prescribed difference between the new AV interval of an adjustment sequence and said AR interval in the event said adjustment sequence begins a second time within a defined time period.

20. A method of operating a dual-chamber pacemaker to avoid fusion between a ventricular stimulus (V-pulse) and an R-wave, said pacemaker having means for sensing atrial activity, means for sensing an R-wave and means for generating said V-pulse; and control means for defining said AV interval as the longest time interval the pacemaker will allow from the occurrence of atrial activity until the generation of a V-pulse, the occurrence of an R-wave during said AV interval causing the generation of a V-pulse to be inhibited; said method comprising the steps of:

(a) generating an A-pulse in the atrium in the absence of said sensed atrial activity;

(b) adjusting said AV interval from its present value to an adjustment start value;

(c) incrementally adjusting the value of said AV interval from its adjustment start value in a direction back towards said first value in prescribed increments, with each prescribed increment comprising a specified change in the duration of said AV interval in the adjustment direction, and with each adjusted value of said AV interval being used in a specified incremental time period that includes at least one cardiac cycle;

(d) monitoring for ventricular activity during each of said specified incremental time periods, said activity comprising either an R-wave and the presence of a V-pulse;

(e) detecting the approximate duration of an AR interval from the monitoring performed in step (d), said AR interval defining the time period between atrial activity and the occurrence of an R-wave;

(f) setting the final value of said AV interval to be different from the AR interval detected in step (e); and (g) generating a V-pulse in the absence of a sensed R-wave during said AV interval;

whereby said AV interval is automatically adjusted to a value that avoids fusion between said V-pulse and said R-wave.

21. The method, as set forth in claim 20, wherein step (e) comprises detecting whether said ventricular activity during the most recent incremental time period is different from said ventricular activity from the incremental time period immediately preceding said most recent incremental time period, whereby the approximate value of said AR interval is known to lie between the value of the AV interval used in the most recent incremental time period and the value of the AV interval used in the immediately preceding incremental time period when said detecting indicates a difference.

22. The method, as set forth in claim 21, wherein step (f) comprises setting the final value of the AV interval to be equal to the AV interval value used in the most recent incremental time period modified by a prescribed margin value.

23. A method of adjusting the AV interval of a dual-chamber pacemaker, said pacemaker including atrial pulse generation means for generating an atrial stimulation pulse (A-pulse), ventricular pulse generation means for generating a ventricular stimulation pulse (V-pulse),

UNITED STATES PATENT AND TRADEMARK OFFICE
CERTIFICATE OF CORRECTION

PATENT NO. : 5,334,220

DATED : August 2, 1994

INVENTOR(S) : Jason A. Sholder

It is certified that error appears in the above-indentified patent and that said Letters Patent is hereby corrected as shown below:

In column 6, line 66, delete "It thus" and substitute therefor --It is thus--.

In Claim 1, column 26, line 58, delete ", and;" and substitute therefor --;--.

In Claim 6, column 28, line 31, delete "(amended)" and substitute therefor --The--.

In Claim 7, column 28, line 34, delete "implant able" and substitute therefor --implantable--.

In Claim 14, column 29, line 11, delete "activity in an atrial channel;' and substitute therefor --activity;--.

In Claim 14, column 29, line 27, delete "forth" and substitute therefor --fourth--.

In Claim 15, column 29, lines 47-48, delete "activity, i.e., an R-wave or a that" and substitute therefor --activity that--.

UNITED STATES PATENT AND TRADEMARK OFFICE
CERTIFICATE OF CORRECTION

PATENT NO. : 5,334,220
DATED : August 2, 1994
INVENTOR(S) : Jason A. Sholder

It is certified that error appears in the above-indentified patent and that said Letters Patent is hereby corrected as shown below:

In Claim 17, column 29, line 59, delete "wherein" and substitute therefor --further comprising means for defining--.

In Claim 17, column 29, lines 59-60, delete "sequence comprises" and substitute therefor --sequence, said means for defining comprising--.

In Claim 23, column 32, line 5, delete the word "and".

In Claim 23, column 32, line 17, please insert the word --and-- following "interval;".

Signed and Sealed this

Sixteenth Day of July, 199

Attest:

BRUCE LEHMAN

Attesting Officer  Commissioner of Patents and Trademarks